(12) United States Patent
Harris et al.

(10) Patent No.: US 6,251,940 B1
(45) Date of Patent: Jun. 26, 2001

(54) INFLAMMATORY CELL INHIBITORS

(75) Inventors: Stephen John Harris; Dominic John Corkill, both of Cowley (GB)

(73) Assignee: British Biotech Pharmaceuticals Ltd., Oxford (GB)

( * ) Notice: Subject to any disclaimer, the term of this patent is extended or adjusted under 35 U.S.C. 154(b) by 0 days.

(21) Appl. No.: 09/355,002

(22) PCT Filed: Mar. 5, 1999

(86) PCT No.: PCT/GB99/00663

§ 371 Date: Jul. 21, 1999

§ 102(e) Date: Jul. 21, 1999

(87) PCT Pub. No.: WO99/44602

PCT Pub. Date: Sep. 10, 1999

(30) Foreign Application Priority Data

Mar. 7, 1998 (GB) .................................................. 9804777

(51) Int. Cl.$^7$ .................................................. A61K 31/215
(52) U.S. Cl. ....................... 514/507; 514/547; 514/430; 514/431; 514/432; 514/315; 514/401
(58) Field of Search .................... 514/507, 547, 514/430, 431, 315, 401, 332

(56) References Cited

FOREIGN PATENT DOCUMENTS

| 0 082 088 | * | 6/1983 | (EP) | ..................................... | 514/507 |
| 0 423 943 | * | 4/1991 | (EP) | ..................................... | 514/507 |
| 94/10990 | * | 5/1974 | (WO) | ..................................... | 514/507 |
| 96/33166 | * | 10/1996 | (WO) | ..................................... | 514/507 |
| 97/49674 | * | 12/1997 | (WO) | ..................................... | 514/507 |
| 98/11063 | * | 3/1998 | (WO) | ..................................... | 514/507 |

* cited by examiner

Primary Examiner—James H. Reamer
(74) Attorney, Agent, or Firm—Greenberg Traurig LLP

(57) ABSTRACT

Compounds of general formula (I)

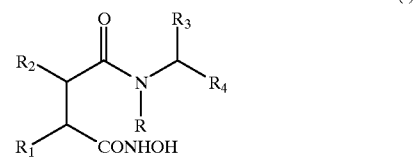

wherein $R_4$ is an ester or thioester group and R, $R_1$, $R_2$, and $R_3$ are as specified in the description, inhibit monocyte and/or macrophage and/or lymphocyte activation and lymphocyte proliferation.

22 Claims, No Drawings

INFLAMMATORY CELL INHIBITORS

This application is a 371 of PTC/GB99/00663, Mar. 5, 1999.

The present invention relates to the use of certain esters and thioesters for the treatment of diseases responsive to inhibition of monocyte and/or macrophage and/or lymphocyte activation and of lymphocyte proliferation.

BACKGROUND TO THE INVENTION

Inflammatory diseases represent a large and increasing health burden throughout the world. Chronic inflammatory conditions include autoimmune disorders (rheumatoid arthritis, multiple sclerosis, psoriasis), allergies, periodontists and gastrointestinal inflammatory diseases. These diseases are characterised by an influx of inflammatory cells into the extravascular connective tissue of target organs. In these sites, aberrant activation of circulating and/or resident lymphocytes becomes self-perpetuating and this leads to chronic tissue destruction. The main cells responsible for this destruction are lymphocytes and monocyte/macrophages. This type of inflammation may also be generated by persistent infection (e.g., tuberculosis), in chronic rejection of solid organ transplants and in chronic graft-versus-host disease following bone marrow transplantation.

The recruitment and accumulation of these cells into the target site is regulated by the release of soluble chemokines and by specific adhesion molecules expressed on the extravascular tissues and on the migrating lymphoid/myeloid cells. Activation of macrophages and the proliferation of lymphocytes, particularly T lymphocytes, within these sites leads to the production of pro-inflammatory molecules; chemokines, cytokines, enzymes, reactive oxygen species (ROS), leukotrienes and prostaglandins.

Chemokines such as RANTES, MIP-1alpha/beta, MIP-3alpha/beta, MCP-1 to MCP-4, TARC, PARC, lymphotactin and fractalkine are released at inflammatory sites and recruit monocytes and T cells. Cytokines such as TNF, INFgamma, IL-1beta, IL-2, IL-12 and IL-18 are released which drive cell proliferation. Multiple enzymes are activated in these inflammatory cells and these include LTA4 hydrolase, 5-LO, COX-2 and PLA-2. Tissue-degrading enzymes such as metalloproteases and cysteine proteases are also released. Gene expression of many of these molecules is regulated by the ubiquitous transcription factor NFkB. The anti-inflammatory activity of steroids is largely through inhibition of activated NFkB but they also affect other pathways which results in toxic side effects. There are various modes of treatment for chronic inflammatory conditions but they largely consist of using a non-steroidal anti-inflammatory agent initially followed up by steroids, cyclosporin/FK506 or, in severe conditions, nucleoside synthesis inhibitors and alkylating agents.

In addition to chronic inflammatory diseases, there are several clinically-important conditions associated with acute inflammation. These include acute respiratory distress syndrome (ARDS), pancreatitis and the allergic conditions of rhinitis and urticaria. Acute transplant rejection and graft-versus-host disease are also a result of rapid inflammatory responses. Lymphocytes are important in priming many acute inflammatory responses due to antibody production (IgE, complement fixing IgG or IgM) and cytokine production but granulocytes and mast cells tend to play a more direct role in the pathogenesis. Monocyte products also drive acute inflammation.

Agents which can inhibit monocyte/macrophage and lymphocyte activation and subsequent lymphocyte proliferation would be useful in treating inflammatory disorders. Such agents would reduce the number of cells in the inflammatory site and the levels of pro-inflammatory mediators.

BRIEF DESCRIPTION OF THE INVENTION

This invention is based on the finding that certain esters and thioesters have these properties, and are therefore of use for the treatment of chronic and acute inflammatory conditions responsive to such inhibiton. Chronic and acute inflammatory conditions include autoimmune disorders (eg rheumatoid arthritis, multiple sclerosis, psoriasis), allergies, periodontists, gastrointestinal inflammatory diseases, acute respiratory distress syndrome (ARDS), pancreatitis, the allergic conditions of rhinitis and urticaria, transplant rejection and graft-versus-host disease.

In our earlier international patent application PCT/GB97/02398 (WO 98/11063), there is disclosed the use of the same class of esters and thioesters as inhibitors of the proliferation of rapidly dividing cells, and thus as agents for the treatment, inter alia, of cancer. However, the present utility as inhibitors of monocyte and/or macrophage and/or lymphocyte activation and of lymphocyte proliferation is unrelated to and not predictable from the teaching of that application.

A few patent publications (WO 92/09563, U.S. Pat. 5,183,900, U.S. Pat. 5,270,326, EP-A-0489577, EP-A-0489579, WO 93/09097, WO 93/24449, WO 94/25434, WO 94/25435, WO 95/04033, WO 95/19965, and WO 95/22966) include within their generic disclosure carboxylate ester compounds having matrix metalloproteinase inhibitory activity. In accordance with the present invention, such compounds are now recognised to have activity as inhibitors of monocyte and/or macrophage and/or lymphocyte activation and of lymphocyte proliferation, but that activity is not suggested by, or predictable from, those publications.

WO 95/04033 discloses $N^4$-hydroxy-N'-(1-(S)-methoxycarbonyl-2,2-dimethylpropyl)-2-(R)-(4-chlorophenylpropyl)succinamide as an intermediate for the preparation of the corresponding methylamide MMP inhibitor. In addition, *Int. J. Pept. Protein Res.* (1996), 48(2), 148–155 discloses the compound

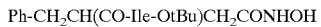

as an intermediate in the preparation of compounds which are inhibitors of neurotensin-degrading enzymes. However, those two appear to be the only specific known carboxylate ester compounds of the kind with which this invention is concerned.

DETAILED DESCRIPTION OF THE INVENTION

In its broadest aspect, the present invention provides a method for treatment of mammals suffering diseases responsive to inhibition of monocyte and/or macrophage and/or lymphocyte activation and of lymphocyte proliferation, comprising administering to the mammal suffering such disease an amount of a compound of general formula (I) or a pharmaceutically acceptable salt hydrate or solvate thereof sufficient to inhibit such activity:

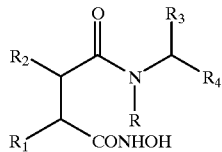

(I)

wherein
R is hydrogen or ($C_1$–$C_6$)alkyl;
$R_1$ is hydrogen;
  ($C_1$–$C_6$)alkyl;
  ($C_2$–$C_6$)alkenyl;
  phenyl or substituted phenyl;
  phenyl ($C_1$–$C_6$)alkyl or substituted phenyl($C_1$–$C_6$) alkyl;
  phenyl ($C_2$–$C_6$)alkenyl or substituted phenyl($C_2$–$C_6$) alkenyl
  heterocyclyl or substituted heterocyclyl;
  heterocyclyl($C_1$–$C_6$)alkyl or substituted heterocyclyl ($C_1$–$C_6$)alkyl;
  a group $BSO_nA$- wherein n is 0, 1 or 2 and B is hydrogen or a ($C_1$–$C_6$) alkyl,
  phenyl, substituted phenyl, heterocyclyl substituted heterocyclyl, ($C_1$–$C_6$)acyl, phenacyl or substituted phenacyl group, and A represents ($C_1$–$C_6$)alkylene;
  hydroxy or ($C_1$–$C_6$)alkoxy;
  amino, protected amino, acylamino, ($C_1$–$C_6$) alkylamino or di-($C_1$–$C_6$)alkylamino;
  mercapto or ($C_1$–$C_6$)alkylthio;
  amino($C_1$–$C_6$)alkyl, ($C_1$–$C_6$)alkylamino($C_1$–C6)alkyl, di($C_1$–$C_6$)alkylamino($C_1$–$C_6$)alkyl, hydroxy($C_1$–$C_6$) alkyl, mercapto($C_1$–$C_6$)alkyl or carboxy($C_1$–$C_6$) alkyl wherein the amino-, hydroxy-, mercapto- or carboxyl-group are optionally protected or the carboxyl-group amidated;
  lower alkyl substituted by carbamoyl, mono(lower alkyl)carbamoyl, di(lower alkyl)carbamoyl, di(lower alkyl)amino, or carboxy-lower alkanoylamino; or
  a cycloalkyl, cycloalkenyl or non-aromatic heterocyclic ring containing up to 3 heteroatoms, any of which may be (i) substituted by one or more substituents selected from $C_1$–$C_6$ alkyl, $C_2$–$C_6$ alkenyl, halo, cyano (—CN), —$CO_2H$, —$CO_2R$, —$CONH_2$, —CONHR, —CON(R)$_2$, —OH, —OR, oxo-, —SH, —SR, —NHCOR, and —$NHCO_2R$ wherein R is $C_1$–$C_6$ alkyl or benzyl and/or (ii) fused to a cycloalkyl or heterocyclic ring;
$R_2$ is a $C_1$–$C_{12}$ alkyl,
  $C_2$–$C_{12}$ alkenyl,
  $C_2$–$C_{12}$ alkynyl,
  phenyl($C_1$–$C_6$ alkyl)-,
  heteroaryl($C_1$–$C_6$ alkyl)-,
  phenyl($C_2$–$C_6$ alkenyl)-,
  heteroaryl($C_2$–$C_6$ alkenyl)-,
  phenyl($C_2$–$C_6$ alkynyl)-,
  heteroaryl($C_2$–$C_6$ alkynyl)-,
  cycloalkyl($C_1$–$C_6$ alkyl)-,
  cycloalkyl($C_2$–$C_6$ alkenyl)-,
  cycloalkyl($C_2$–$C_6$ alkynyl)-,
  cycloalkenyl($C_1$–$C_6$ alkyl)-,
  cycloalkenyl($C_2$–$C_6$ alkenyl)-,
  cycloalkenyl($C_2$–$C_6$ alkynyl)-,
  phenyl($C_1$–$C_6$ alkyl)O($C_1$–$C_6$ alkyl)-, or
  heteroaryl($C_1$–$C_6$ alkyl)O($C_1$–$C_6$ alkyl)-group,
  any one of which may be optionally substituted by
    $C_1$–$C_6$ alkyl,
    $C_1$–$C_6$ alkoxy,
    halo,
    cyano (—CN),
    phenyl or heteroaryl, or
    phenyl or heteroaryl substituted by
      $C_1$–$C_6$ alkyl,
      $C_1$–$C_6$ alkoxy,
      halo, or
      cyano (—CN);
  $R_3$ is the characterising group of a natural or non-natural a amino acid in which any functional groups may be protected; and
  $R_4$ is an ester or thioester group,
or a pharmaceutically acceptable salt, hydrate or solvate thereof.

In another broad aspect of the invention, there is provided the use of a compound of formula (I) as defined in the immediately preceding paragraph, in the preparation of a pharmaceutical composition treatment of mammals suffering diseases responsive to inhibition of monocyte and/or macrophage and/or lymphocyte activation and of lymphocyte proliferation.

In one particular aspect of the invention, the compound used is one of general formula (I) above wherein R, $R_1$, $R_2$, $R_3$ and $R_4$ are as defined above with reference to formula (I), or a pharmaceutically acceptable salt, hydrate or solvate thereof, PROVIDED THAT:
  (i) when R and $R_1$ are hydrogen, $R_2$ is 4-chlorophenylpropyl, and $R^3$ is tert-butyl, then $R_4$ is not a methyl carboxylate ester group; and
  (ii) when R and $R_1$ are hydrogen, $R_2$ is phenylmethyl, and $R^3$ is 1-methylprop-1-yl, then $R_4$ is not a tert-butyl carboxylate ester group.

In another particular aspect of the invention, the compound used is one of general formula (I) above wherein:
  R, $R_1$ and $R_4$ are as defined above with reference to formula (I)
  $R_2$ is $C_1$–$C_{12}$ alkyl, $C_2$–$C_{12}$ alkenyl, $C_2$–$C_{12}$ alkynyl, biphenyl($C_1$–$C_6$ alkyl)-, phenylheteroaryl($C_1$–$C_6$ alkyl)-, heteroarylphenyl($C_1$–$C_6$ alkyl)-, biphenyl($C_2$–$C_6$ alkenyl)-, phenylheteroaryl($C_2$–$C_6$ alkenyl)-, heteroarylphenyl($C_2$–$C_6$ alkenyl)-, phenyl($C_2$–$C_6$ alkynyl)-, heteroaryl($C_2$–$C_6$ alkynyl)-, biphenyl($C_2$–$C_6$ alkynyl)-, phenylheteroaryl($C_2$–$C_6$ alkynyl)-, heteroarylphenyl($C_2$–$C_6$ alkynyl)-, phenyl($C_1$–$C_6$ alkyl)O($C_1$–$C_6$ alkyl)-, or heteroaryl ($C_1$–$C_6$ alkyl)O($C_1$–$C_6$ alkyl)-,
    any one of which may be optionally substituted on a ring carbon atom by $C_1$–$C_6$ alkyl, $C_1$–$C_6$ alkoxy, halo, or cyano (—CN); and
  $R_3$ is $C_1$–$C_6$ alkyl, optionally substituted benzyl, optionally substituted phenyl, optionally substituted heteroaryl; or
    the characterising group of a natural a amino acid, in which any functional group may be protected, any amino group may be acylated and any carboxyl group present may be amidated; or
    a heterocyclic($C_1$–$C_6$)alkyl group, optionally substituted in the heterocyclic ring;
and pharmaceutically acceptable salts, hydrates or solvates thereof.

As used herein the term "($C_1$–$C_6$)alkyl" or "lower alkyl" means a straight or branched chain alkyl moiety having from 1 to 6 carbon atoms, including for example, methyl, ethyl, n-propyl, isopropyl, n-butyl, isobutyl, sec-butyl, t-butyl, n-pentyl and n-hexyl.

The term "($C_2$–$C_6$)alkenyl" means a straight or branched chain alkenyl moiety having from 2 to 6 carbon atoms having at least one double bond of either E or Z stereochemistry where applicable. This term would include, for example, vinyl, allyl, 1- and 2-butenyl and 2-methyl-2-propenyl.

The term "$C_2$–$C_6$ alkynyl" refers to straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

The term "cycloalkyl" means a saturated alicyclic moiety having from 3–8 carbon atoms and includes, for example, cyclohexyl, cyclooctyl, cycloheptyl, cyclopentyl, cyclobutyl and cyclopropyl.

The term "cycloalkenyl" means an unsaturated alicyclic moiety having from 4–8 carbon atoms and includes, for example, cyclohexenyl, cyclooctenyl, cycloheptenyl, cyclopentenyl, and cyclobutenyl. In the case of cycloalkenyl rings of from 5–8 carbon atoms, the ring may contain more than one double bond.

The term "aryl" means an unsaturated aromatic carbocyclic group which is moncyclic (eg phenyl) or polycyclic (eg naphthyl).

The unqualified term "heterocyclyl" or "heterocyclic" means (i) a 5–7 membered heterocyclic ring containing one or more heteroatoms selected from S, N and O, and optionally fused to a benzene ring, including for example, pyrrolyl, furyl, thienyl, piperidinyl, imidazolyl, oxazolyl, thiazolyl, thiadiazolyl, pyrazolyl, pyridinyl, pyrrolidinyl, pyrimidinyl, morpholinyl, piperazinyl, indolyl, benzimidazolyl, maleimido, succinimido, phthalimido, 1,2-dimethyl-3,5-dioxo-1,2,4-triazolidin4-yl, 3,4,4-trimethyl-2,5-dioxo-1-imidazolidinyl, 2-methyl-3,5-dioxo-1,2,4-oxadiazol4-yl, 3-methyl-2,4,5-trioxo-1-imidazolidinyl, 2,5-dioxo-3-phenyl-1-imidazolidinyl, 2-oxo-1-pyrrolidinyl, 2,5-dioxo-1-pyrrolidinyl or 2,6-dioxopiperidinyl, or (ii) a naphththalimido (ie 1,3-dihydro-1,3-dioxo-2H-benz[f]isoindol-2-yl), 1,3-dihydro-1-oxo-2H-benz[f]isoindol-2-yl, 1,3-dihydro-1, 3-dioxo-2H-pyrrolo[3,4-b]quinolin-2-yl, or 2,3-dihydro-1, 3-dioxo-1H-benz[d,e]isoquinolin-2-yl group.

The term "heteroaryl" means a 5–7 membered substituted or unsubstituted aromatic heterocycle containing one or more heteroatoms. Illustrative of such rings are thienyl, furyl, pyrrolyl, imidazolyl, thiazolyl, pyrazolyl, isoxazolyl, isothiazolyl, trizolyl, thiadiazolyl, oxadiazolyl, pyridinyi, pyridazinyl, pyrimidinyl, pyrazinyl and triazinyl.

The term "ester" or "esterified carboxyl group" means a group $R_9O(C=O)$— in which $R_9$ is the group characterising the ester, notionally derived from the alcohol $R_9OH$.

The term "thioester" means a group $R_9S(C=O)$— or $R_9S(C=S)$— or $R_9O(C=S)$— in which $R_9$ is the group characterising the thioester, notionally derived from the alcohol $R_9OH$ or the thioalcohol $R_9SH$.

Unless otherwise specified in the context in which it occurs, the term "substituted" as applied to any moiety herein means substituted with up to four substituents, each of which independently may be ($C_1$–$C_6$)alkyl, ($C_1$–$C_6$) alkoxy, hydroxy, mercapto, ($C_1$–$C_6$)alkylthio, amino, halo (including fluoro, chloro, bromo and iodo), nitro, trifluoromethyl, —COOH, —CONH$_2$, —CN, —COOR$^A$, —CONHR$^A$ or —CONHR$^A$R$^A$ wherein R$^A$ is a ($C_1$–$C_6$) alkyl group or the residue of a natural alpha-amino acid.

The term "side chain of a natural or non-natural alpha-amino acid" means the group R$^1$ in a natural or non-natural amino acid of formula NH$_2$—CH(R$^1$)—COOH.

Examples of side chains of natural alpha amino acids include those of alanine, arginine, asparagine, aspartic acid, cysteine, cystine, glutamic acid, histidine, 5-hydroxylysine, 4-hydroxyproline, isoleucine, leucine, lysine, methionine, phenylalanine, proline, serine, threonine, tryptophan, tyrosine, valine, α-aminoadipic acid, α-amino-n-butyric acid, 3,4-dihydroxyphenylalanine, homoserine, α-methylserine, ornithine, pipecolic acid, and thyroxine.

Natural alpha-amino acids which contain functional substituents, for example amino, carboxyl, hydroxy, mercapto, guanidyl, imidazolyl, or indolyl groups in their characteristic side chains include arginine, lysine, glutamic acid, aspartic acid, tryptophan, histidine, serine, threonine, tyrosine, and cysteine. When $R_3$ in the compounds of the invention is one of those side chains, the functional substituent may optionally be protected.

The term "protected" when used in relation to a functional substituent in a side chain of a natural alpha-amino acid means a derivative of such a substituent which is substantially non-functional. For example, carboxyl groups may be esterified (for example as a $C_1$–$C_6$ alkyl ester), amino groups may be converted to amides (for example as a NHCOC$_1$–$C_6$ alkyl amide) or carbamates (for example as an NHC(=O) OC$_1$–$C_6$ alkyl or NHC(=O)OCH$_2$Ph carbamate), hydroxyl groups may be converted to ethers (for example an OC$_1$–$C_6$ alkyl or a O($C_1$–$C_6$ alkyl)phenyl ether) or esters (for example a OC(=O)C$_1$–$C_6$ alkyl ester) and thiol groups may be converted to thioethers (for example a tert-butyl or benzyl thioether) or thioesters (for example a SC(=O)C$_1$–$C_6$ alkyl thioester).

Examples of side chains of non-natural alpha amino acids include those referred to below in the discussion of suitable $R_3$ groups for use in compounds of the present invention.

Salts of the compounds used in the invention include physiologically acceptable acid addition salts for example hydrochiorides, hydrobromides, sulphates, methane sulphonates, p-toluenesulphonates, phosphates, acetates, citrates, succinates, lactates, tartrates, fumarates and maleates. Salts may also be formed with bases, for example sodium, potassium, magnesium, and calcium salts.

There are several chiral centres in the compounds used according to the invention because of the presence of asymmetric carbon atoms. The presence of several asymmetric carbon atoms gives rise to a number of diastereomers with R or S stereochemistry at each chiral centre. For example, in the compounds used in the invention, the C atom carrying the hydroxamic acid and $R_1$ groups may be in the R or S configuration, the C atom carrying the $R_2$ group may be predominantly in the R configuration, and the C atom carrying the $R_3$ and $R_4$ groups may be in either the R or S configuration, with the predominantly S configuration presently preferred.

As mentioned above, compounds of formula (I) above, are useful in human or veterinary medicine since they inhibit monocyte/macrophage and lymphocyte activation and subsequent lymphocyte proliferation. They are therefore useful for the treatment of chronic and acute inflammatory conditions, including autoimmune disorders (eg rheumatoid arthritis, multiple sclerosis, psoriasis), allergies, periodontists, gastrointestinal inflammatory diseases, acute respiratory distress syndrome (ARDS), pancreatitis, the allergic conditions of rhinitis and urticaria, acute transplant rejection and graft-versus-host disease.

The compounds with which the invention is concerned may be prepared for administration by any route consistent with their pharmacokinetic properties.

Orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

Clinically safe and effective dosages for the compounds with which the invention is concerned will be determined by clinical trials, as is required by the regulatory authorities in the art. It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

In the compounds used in the invention, examples of substituents R, to $R_4$ are given below:

The group $R_1$ $R_1$ may be, for example, hydrogen, methyl, ethyl, n-propyl, n-butyl, isobutyl, hydroxyl, methoxy, allyl, phenylpropyl, phenylprop-2-enyl, thienylsulphanylmethyl, thienylsulphinylmethyl, or thienylsulphonylmethyl; or $C_1$–$C_4$ alkyl,eg methyl, ethyl n-propyl or n-butyl, substituted by a phthalimido, 1,2-dimethyl-3,5-dioxo-1,2,4-triazolidin4-yl, 3-methyl-2,5-dioxo-1-imidazolidinyl, 3,4,4-trimethyl-2,5-dioxo-1-imidazolidinyl, 2-methyl-3,5-dioxo-1,2,4-oxadiazol4-yl, 3-methyl-2,4,5-trioxo-1-imidazolidinyl, 2,5-dioxo-3-phenyl-1-imidazolidinyl, 2-oxo-1-pyrrolidinyl, 2,5-dioxo-1-pyrrolidinyl or 2,6-dioxopiperidinyl, 5,5-dimethyl-2,4-dioxo-3-oxazolidinyl, hexahydro-1,3-dioxopyrazolo[1,2,a] [1,2,4]-triazol-2-yl, or a naphththalimido (ie 1,3-dihydro-1,3-dioxo-2H-benz[f]isoindol-2-yl), 1,3-dihydro-1-oxo-2H-benz[f]isoindol-2-yl, 1,3-dihydro-1,3-dioxo-2H-pyrrolo[3,4-b]quinolin-2-yl, or 2,3-dihydro-1,3-dioxo-1H-benz[d,e]isoquinolin-2-yl group; or cyclohexyl, cyclooctyl, cycloheptyl, cyclopentyl, cyclobutyl, cyclopropyl, tetrahydropyranyl or morpholinyl.

Presently preferred $R_1$ groups include n-propyl, allyl, hydroxy, methoxy and thienylsulfanylmethyl.

The group $R_2$ $R_2$ may for example be $C_1$–$C_{12}$ alkyl, $C_3$–$C_6$ alkenyl or $C_3$–$C_6$ alkynyl;

phenyl($C_1$–$C_6$ alkyl)-, phenyl($C_3$–$C_6$ alkenyl)- or phenyl($C_3$–$C_6$ alkynyl)- optionally substituted in the phenyl ring;

heteroaryl($C_1$–$C_6$ alkyl)-, heteroaryl($C_3$–$C_6$ alkenyl)- or heteroaryl($C_3$–$C_6$ alkynyl)- optionally substituted in the heteroaryl ring;

4-phenylphenyl($C_1$–$C_6$ alkyl)-, 4-phenylphenyl($C_3$–$C_6$ alkenyl)-, 4-phenylphenyl($C_3$–$C_6$ alkynyl)-, 4-heteroarylphenyl($C_1$–$C_6$ alkyl)-, 4-heteroarylphenyl($C_3$–$C_6$ alkenyl)-, 4-heteroarylphenyl($C_3$–$C_6$ alkynyl)-, optionally substituted in the terminal phenyl or heteroaryl ring;

phenoxy($C_1$–$C_6$ alkyl)- or heteroaryloxy($C_1$–$C_6$ alkyl)- optionally substituted in the phenyl or heteroaryl ring;

Specific examples of such groups include methyl, ethyl, n- and iso-propyl, n-, iso- and tert-butyl, n-pentyl, n-hexyl, n-heptyl, n-nonyl, n-decyl, prop-2-yn-1-yl, 3-phenylprop-2-yn-1-yl, 3-(2-chlorophenyl)prop-2-yn-1-yl, phenylpropyl, 4-chlorophenylpropyl, 4-methylphenylpropyl, 4-methoxyphenylpropyl, phenoxybutyl, 3-(4-pyridylphenyl)propyl-, 3-(4-(4-pyridyl)phenyl)prop-2-yn-1-yl, 3-(4-phenylphenyl)propyl-, 3-(4-phenyl)phenyl)prop-2-yn-1-yl and 3-[(4-chlorophenyl)phenyl]propyl-, cyclopentylmethyl, and benzyl.

Presently preferred $R_2$ groups include n- and iso-butyl, n-hexyl, cyclopentylmethyl, benzyl, and 3-(2-chlorophenyl)prop-2-yn-1-yl.

The group $R_3$ $R_3$ may for example be $C_1$–$C_6$ alkyl, phenyl, 2, -3-, or 4-hydroxyphenyl, 2, -3-, or 4-methoxyphenyl, 2- or 3-thienyl, 2, -3-, or 4-pyridylmethyl, benzyl, 2, -3-, or 4-hydroxybenzyl, 2, -3-, or 4-benzyloxybenzyl, 2, -3-, or 4-$C_1$–$C_6$ alkoxybenzyl, or benzyloxy($C_1$–$C_6$alkyl)-group; or the characterising group of a natural α amino acid, in which any functional group may be protected, any amino group may be acylated and any carboxyl group present may be amidated; or a group -[Alk]$_n$$R_6$ where Alk is a ($C_1$–$C_6$)alkyl or ($C_2$–$C_6$)alkenyl group optionally interrupted by one or more —O—, or —S— atoms or —N($R_7$)— groups [where $R_7$ is a hydrogen atom or a ($C_1$–$C_6$) alkyl group], n is 0 or 1, and $R_6$ is an optionally substituted cycloalkyl or cycloalkenyl group; or a benzyl group substituted in the phenyl ring by a group of formula —OCH$_2$COR$_8$ where $R_8$ is hydroxyl, amino, ($C_1$–$C_6$)alkoxy, phenyl($C_1$–$C_6$)alkoxy, ($C_1$–$C_6$)alkylamino, di(($C_1$–$C_6$)alkyl)amino, phenyl ($C_1$–$C_6$)alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid; or a heterocyclic($C_1$–$C_6$)alkyl group, either being unsubstituted or mono- or di-substituted in the heterocyclic ring with halo, nitro, carboxy, ($C_1$–$C_6$)alkoxy, cyano, ($C_1$–$C_6$)alkanoyl, trifluoromethyl ($C_1$–$C_6$)alkyl, hydroxy, formyl, amino, ($C_1$–$C_6$)alkylamino, di-($C_1$–$C_6$)alkylamino, mercapto, ($C_1$–$C_6$)alkylthio, hydroxy($C_1$–$C_6$)alkyl, mercapto($C_1$–$C_6$)alkyl or ($C_1$–$C_6$)alkylphenylmethyl; or a group —$CR_aR_bR_c$ in which:

each of $R_a$, $R_b$ and $R_c$ is independently hydrogen, ($C_1$–$C_6$)alkyl, ($C_2$–$C_6$)alkenyl, ($C_2$–$C_6$)alkynyl, phenyl($C_1$–$C_6$)alkyl, ($C_3$–$C_8$)cycloalkyl; or $R_c$ is hydrogen and $R_a$ and $R_b$ are independently phenyl or heteroaryl such as pyridyl; or $R_c$ is hydrogen, ($C_1$–$C_6$)alkyl, ($C_2$–$C_6$)alkenyl, ($C_2$–$C_6$)alkynyl, phenyl($C_1$–$C_6$)alkyl, or ($C_3$–$C_8$) cycloalkyl, and $R_a$ and $R_b$ together with the carbon atom to which they are attached form a 3 to 8 membered cycloalkyl or a 5- to 6-membered heterocyclic ring; or $R_a$, $R_b$ and $R_c$ together with the carbon atom to which they are attached form a tricyclic ring (for example adamantyl); or $R_a$ and $R_b$ are each independently ($C_1$–$C_6$)alkyl, ($C_2$–$C_6$)alkenyl, ($C_2$–$C_6$)alkynyl, phenyl($C_1$–$C_6$) alkyl, or a group as defined for $R_c$ below other than hydrogen, or $R_a$ and $R_b$ together with the carbon atom to which they are attached form a cycloalkyl or heterocyclic ring, and $R_c$ is hydrogen, —OH, —SH, halogen, —CN, —$CO_2H$, ($C_1$–$C_4$)perfluoroalkyl, —$CH_2OH$, —$CO_2$($C_1$–$C_6$)alkyl, —O($C_1$–$C_6$)alkyl, —O($C_2$–$C_6$)alkenyl, —S($C_1$–$C_6$)alkyl, —SO ($C_1$–$C_6$)alkyl, —$SO_2$($C_1$–$C_6$)alkyl, —S($C_2$–$C_6$) alkenyl, —SO($C_2$–$C_6$)alkenyl, —$SO_2$($C_2$–$C_6$) alkenyl or a group —Q-W wherein Q represents a bond or —O—, —S—, —SO—or —$SO_2$— and W represents a phenyl, phenylalkyl, ($C_3$–$C_8$) cycloalkyl, ($C_3$–$C_8$)cycloalkylalkyl, ($C_4$–$C_8$) cycloalkenyl, ($C_4$–$C_8$)cycloalkenylalkyl, heteroaryl or heteroarylalkyl group, which group W may optionally be substituted by one or more substituents independently selected from, hydroxyl, halogen, —CN, —$CO_2H$, —$CO_2$ ($C_1$–$C_6$)alkyl, —$CONH_2$, —CONH($C_1$–$C_6$)alkyl, —CONH($C_1$–$C_6$alkyl$)_2$, —CHO, —$CH_2OH$, ($C_1$–$C_4$)perfluoroalkyl, —O($C_1$–$C_6$)alkyl, —S($C_1$–$C_6$)alkyl, —SO($C_1$–$C_6$)alkyl, —$SO_2$ ($C_1$–$C_6$)alkyl, —$NO_2$, —$NH_2$, —NH($C_1$–$C_6$) alkyl, —N(($C_1$–$C_6$)alkyl$)_2$, —NHCO($C_1$–$C_6$) alkyl, ($C_1$–$C_6$)alkyl, ($C_2$–$C_6$)alkenyl, ($C_2$–$C_6$) alkynyl, ($C_3$–$C_8$)cycloalkyl, ($C_4$–$C_8$)cycloalkenyl, phenyl or benzyl.

Examples of particular $R_3$ groups include benzyl, phenyl, cyclohexylmethyl, pyridin-3-ylmethyl, tert-butoxymethyl, iso-butyl, sec-butyl, tert-butyl, 1-benzylthio-1-methylethyl, 1-methylthio-1-methylethyl, and 1-mercapto-1-methylethyl.

Presently preferred $R_3$ groups include phenyl, benzyl, tert-butoxymethyl and iso-butyl.

The group $R_4$

Examples of particular ester and thioester groups $R_4$ groups include those of formula —(C=O)$OR_9$, —(C=O) $SR_9$, —(C=S)$SR_9$, and —(C=S)$OR_9$, wherein $R_9$ is ($C_1$–$C_6$)alkyl, ($C_2$–$C_6$)alkenyl, cycloalkyl, cycloalkyl ($C_1$–$C_6$)alkyl-, phenyl, heterocyclyl, phenyl($C_1$–$C_6$)alkyl-, heterocyclyl($C_1$–$C_6$)alkyl-, ($C_1$–$C_6$)alkoxy($C_1$–$C_6$)alkyl-, ($C_1$–$C_6$)alkoxy($C_1$–$C_6$)alkoxy($C_1$–$C_6$)alkyl-, any of which may be substituted on a ring or non-ring carbon atom or on a ring heteroatom, if present. Examples of such $R_9$ groups include methyl, ethyl, n-and iso-propyl, n-, sec- and tert-butyl, 1-ethyl-prop-1-yl, 1-methyl-prop-1-yl, 1-methyl-but-1-yl, cyclopentyl, cyclohexyl, allyl, phenyl, benzyl, 2-, 3- and 4-pyridylmethyl, N-methylpiperidin-4-yl, 1-methylcyclopent-1-yl, adamantyl, tetrahydrofuran-3-yl and methoxyethyl.

Presently preferred are compounds of formula (I) wherein $R_4$ is a carboxylate ester of formula —(C=O)$OR_9$, wherein $R_9$ is benzyl, cyclopentyl, isopropyl or tert-butyl.

The group R

Presently preferred R groups are hydrogen and methyl.

Specific compounds for use in accordance with the invention include those of examples 1, 2, 3, 6, 19, 39, 40 and 43.

Compounds used according to the present invention may be prepared by the methods described in our published international patent application No WO 98/11063. Specific examples of compounds which may be used are those of the following examples 1–50. Examples 1–42 are compounds disclosed in WO 98/11063.

EXAMPLE 1 (Example 1 of WO 98/11063)

2S-(3S-Hydroxycarbamoyl-2R-isobutyl-hex-5-enoylamino)-3-phenylpropionic acid methyl ester.

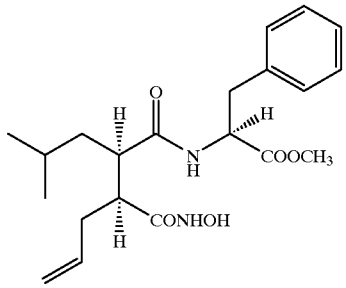

EXAMPLE 2 (Example 2 of WO 98/11063)

2S-(3S-Hydroxycarbamoyl-2R-isobutyl-hex-5-enoylamino)-3-phenylpropionic acid ethyl ester.

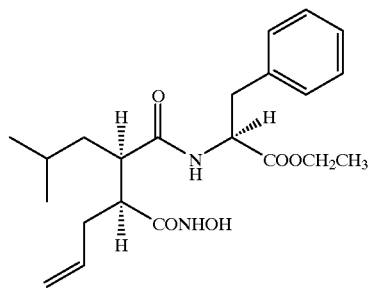

EXAMPLE 3 (Example 3 of WO 98/11063)

2S-(3S-Hydroxycarbamoyl-2R-isobutyl-hex-5-enoylamino)-3-phenylpropionic acid isopropyl ester.

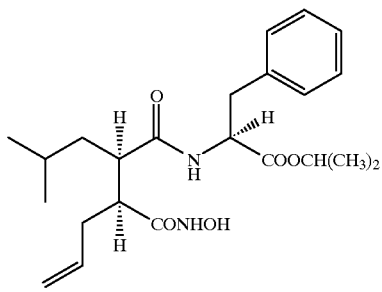

EXAMPLE 4 (Example 5 of WO 98/11063)
3R-(2-Phenyl-1S-methylcarboxy-ethylcarbamoyl)-2S,
5-dimethylhexanohydroxamic acid

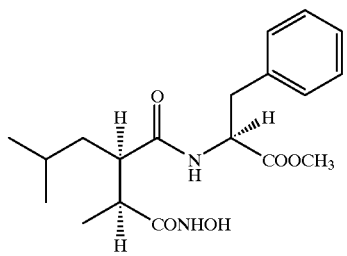

EXAMPLE 5 (Example 6 of WO 98/11063)
2S-(3S-Hydroxycarbamoyl-2R-isobutyl-hex-5-
enoylamino)-3-phenyl-propionic acid tert-butyl ester

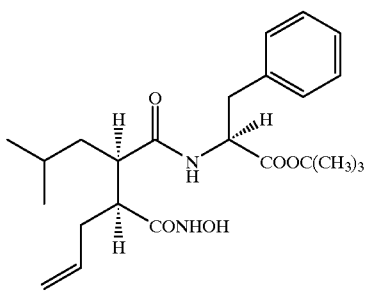

EXAMPLE 6 (Example 7 of WO 98/11063)
2S-(2R-Hydroxycarbamoylmethyl-4-methyl-
pentanoylamino)-3-phenyl-propionic acid isopropyl ester

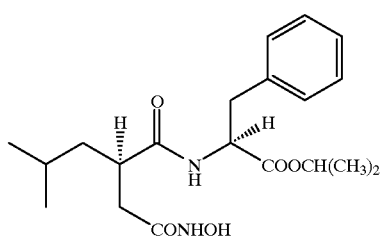

EXAMPLE 7 (Example 8 of WO 98/11063)
2S-[2R-(S-Hydroxy-hydroxycarbamoyl-methyl)-4-methyl-
pentanoylamine]-3-phenyl-propionic acid isopropyl ester.

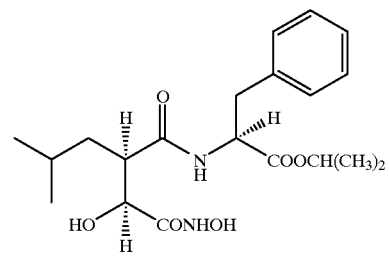

EXAMPLE 8 (Example 9 of WO 98/11063)
2S-[2R-(1S-Hydroxycarbamoyl-ethyl)-4-methyl-
pentanoylamino]-3-phenyl-propionic acid isopropyl ester.

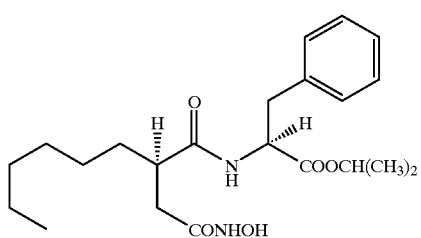

EXAMPLE 9 (Example 10 of WO 98/11063)
2S-(2R-Hydroxycarbamoylmethyl-octanoylamino)-3-
phenyl-propionic acid isopropyl ester.

EXAMPLE 10 (Example 11 of WO 98/11063)
2S-[2R-(S-Hydroxy-hydroxycarbamoyl-methyl)-4-methyl-
pentanoylamino]-3-phenyl-propionic acid cyclopentyl ester.

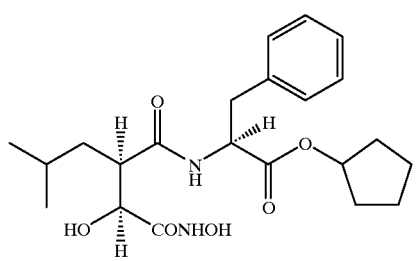

EXAMPLE 11 (Example 12 of WO 98/11063)
2S-(3S-Hydroxycarbamoyl-2R-isobutyl-hex-5-
enoylamino)-3S-methyl-pentanoic acid cyclopentyl ester.

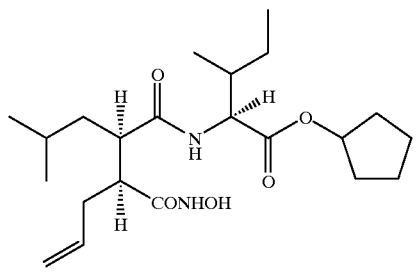

EXAMPLE 12 (Example 13 of WO 98/11063)
2S-(3S-Hydroxycarbamoyl-2R-isobutyl-hex-5-enoylamino)-3-phenylpropionic acid 2-methoxy-ethyl ester.

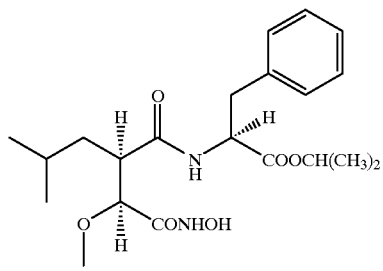

EXAMPLE 16 (Example 17 of WO 98/11063)
2S-{2R-[1S-Hydroxycarbamoyl-2-(thiophen-2-ylsulphanyl)-ethyl]4-methyl-pentanoylamino}-3-phenyl-propionic acid isopropyl ester.

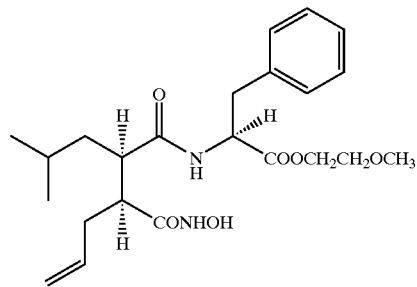

EXAMPLE 13 (Example 1 of WO 98/11063)
2S-[2R-(1S-Hydroxycarbamoyl-ethyl)-4-methyl-pentanoylamino]-3-phenyl-propionic acid 2-methoxy-ethyl ester.

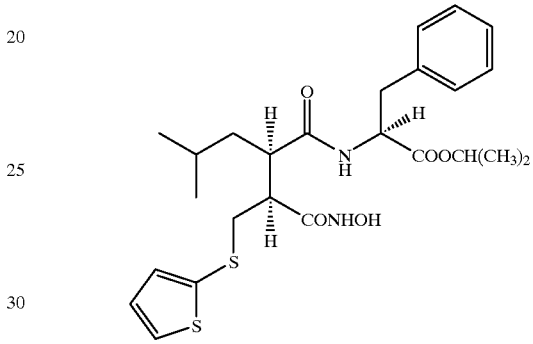

EXAMPLE 17 (Example 18 of WO 98/11063)
2S-[2-R-(1S-Hydroxycarbamoyl-ethyl)-4-methyl-pentanoylamino]-3,3-dimethyl-butyric acid 2-methoxy-ethyl ester.

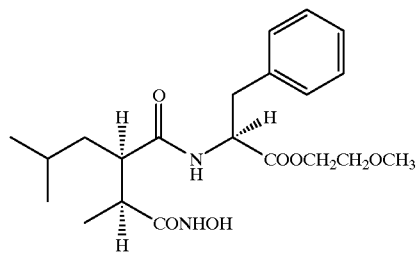

EXAMPLE 14 (Example 15 of WO 98/11063)
2S-(3S-Hydroxycarbamoyl-2R-isobutyl-hexanoylamino)-3,3-dimethyl-butyric acid 2-methoxy-ethyl ester.

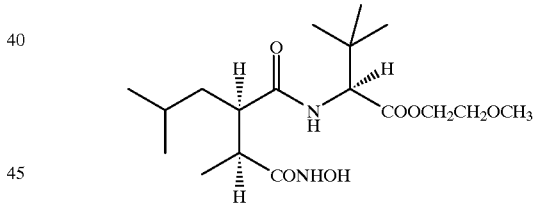

EXAMPLE 18 (Example 19 of WO 98/11063)
2S-(3S-Hydroxycarbamoyl-2R-isobutyl-hex-5-enoylamino)-3,3-dimethyl-butyric acid 2-methoxy-ethyl ester.

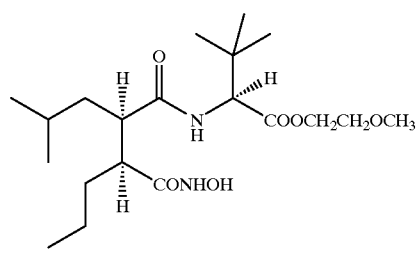

EXAMPLE 15 (Example 1 of WO 98/11063)
2S-[2R-(S-Hydroxycarbamoyl-methoxy-methyl)-4-methyl-pentanoylamino]-3-phenyl-propionic acid isopropyl ester.

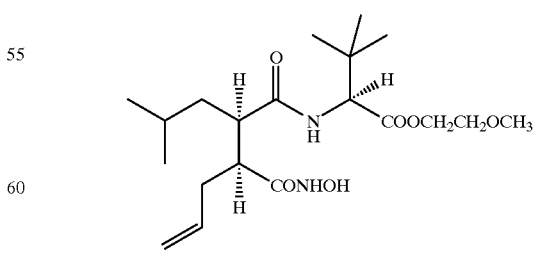

EXAMPLE 19 (Example 20 of WO 98/11063)
2S-(3S-Hydroxycarbamoyl-2R-isobutyl-hex-5-enoylamino)-3-phenylpropionic acid cyclopentyl ester.

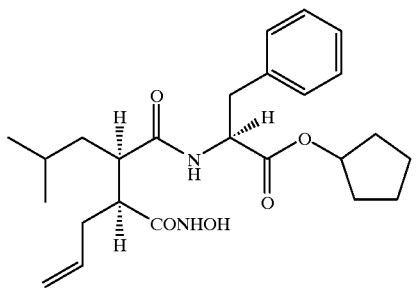

EXAMPLE 20 (Example 21 of WO 98/11063)
2S-(3S-Hydroxycarbamoyl-2R-isobutyl-hexanoylamino)-3-phenylpropionic acid isopropyl ester.

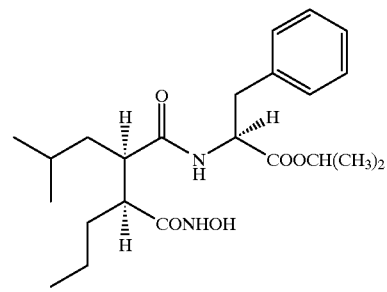

EXAMPLE 21 (Example 22 of WO 98/11063)
2S-(3S-Hydroxycarbamoyl-2R-isobutyl-hex-5-enoylamino)-3,3-dimethyl-butyric acid isopropyl ester.

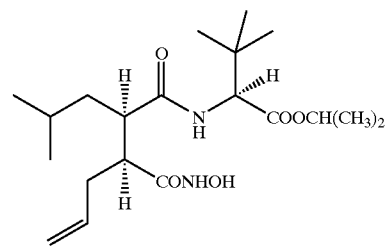

EXAMPLE 22 (Example 23 of WO 98/11063)
2R-(3S-Hydroxycarbamoyl-2R-isobutyl-hex-5-enoylamino)-3-phenylpropionic acid isopropyl ester.

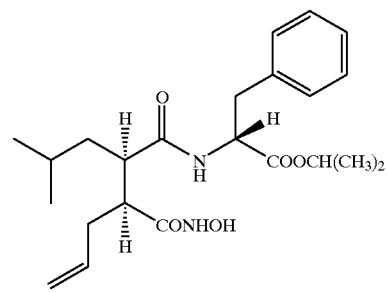

EXAMPLE 23 (Example 24 of WO 98/11063)
2S-[2R-(S-Hydroxycarbamoyl-methoxy-methyl)-4-methyl-pentanoylamino]-3,3-dimethyl-butyric acid isopropyl ester.

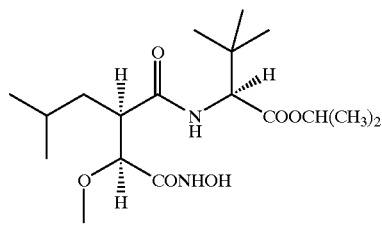

EXAMPLE 24 (Example 25 of WO 98/11063)
2S-{(3S-Hydroxycarbamoyl-2R-isobutyl-hex-5-enoyl)-methyl-amino}-3-phenylpropionic acid isopropyl ester.

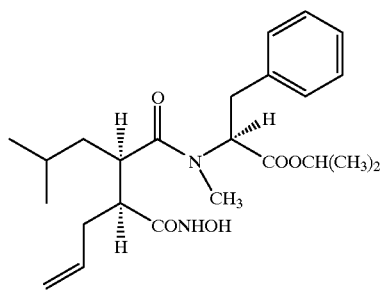

EXAMPLE 25 (Example 26 of WO 98/11063)
2S-(3S-Hydroxycarbamoyl-2R-isobutyl-hex-5-enoylamino)-3-phenylpropionic acid benzyl ester.

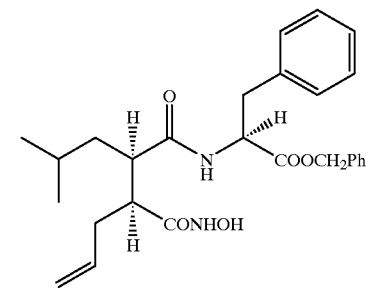

EXAMPLE 26 (Example 27 of WO 98/11063)
2S-(3S-Hydroxycarbamoyl-2R-isobutyl-hex-5-enoylamino)-4-methyl-pentanoic acid cyclopentyl ester.

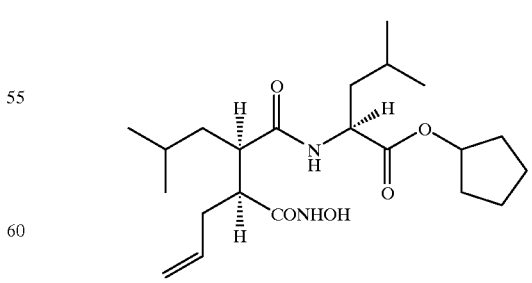

EXAMPLE 27 (Example 28 of WO 98/11063)
3-Cyclohexyl-2S-(3S-hydroxycarbamoyl-2R-isobutyl-hex-5-enoylamino)-propionic acid cyclopentyl ester.

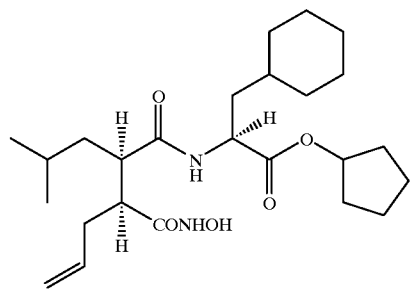

EXAMPLE 28 (Example 29 of WO 98/11063)

2S-(3S-Hydroxycarbamoyl-2R-isobutyl-hex-5-enoylamino)-3-phenylpropionic acid 1-methyl-piperidin-4-yl ester.

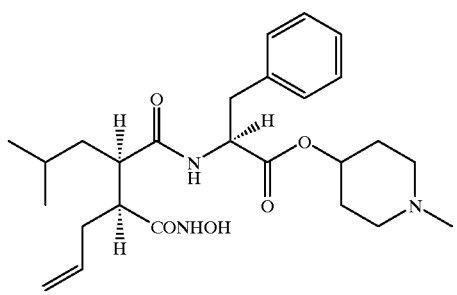

EXAMPLE 29 (Example 30 of WO 98/11063)

2S-(3S-Hydroxycarbamoyl-2R-isobutyl-hex-5-enoylamino)-3-phenylpropionic acid 1-ethyl-propyl ester.

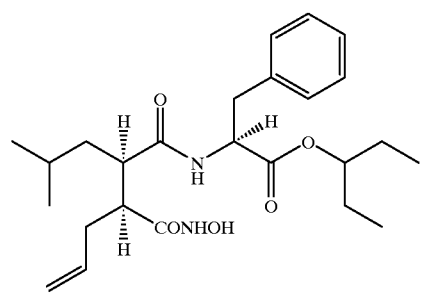

EXAMPLE 30 (Example 31 of WO 98/11063)

2S-(3S-Hydroxycarbamoyl-2R-isobutyl-hex-5-enoylamino)-3-phenylpropionic acid 1S-methyl-butyl ester.

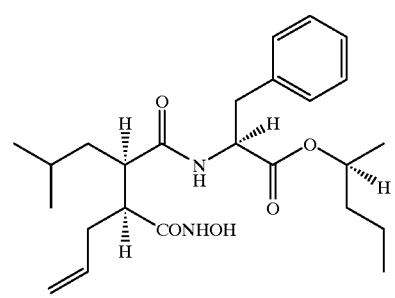

EXAMPLE 31 (Example 32 of WO 98/11063)

2S-(3S-Hydroxycarbamoyl-2R-isobutyl-hex-5-enoylamino)-3-phenylpropionic acid cyclohexyl ester.

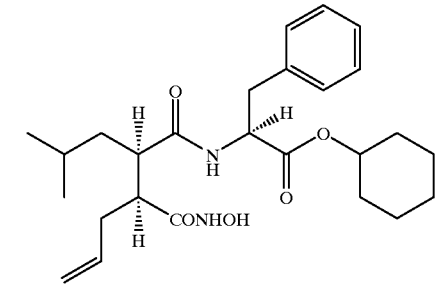

EXAMPLE 32 (Example 1of WO 98/11063)

2S{2R-[1S-Hydroxycarbamoyl-2-(thiophen-2-ylsulphanyl)-ethyl]-4-methyl-pentanoylamino}-3,3-dimethyl-butyric acid isopropyl ester.

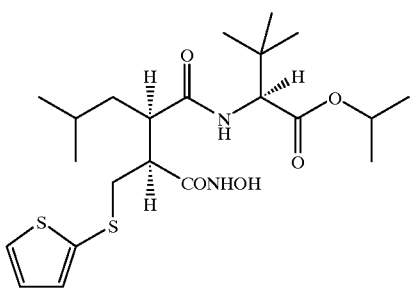

EXAMPLE 33 (Example 34 of WO 98/11063)

2S-(3S-Hydroxycarbamoyl-2R-isobutyl-hex-5-enoylamino)-3-phenylpropionic acid 1R-methyl-butyl ester.

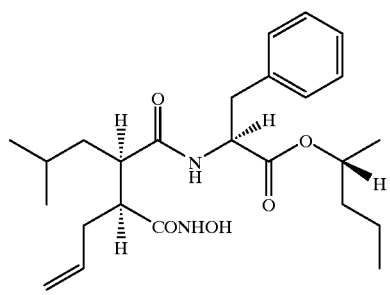

EXAMPLE 34 (Example 35 of WO 98/11063)

2S-(3S-Hydroxycarbamoyl-2R-isobutyl-hex-5-enoylamino)-3-phenylpropionic acid tetrahydro-furan-3(R,S)-yl ester.

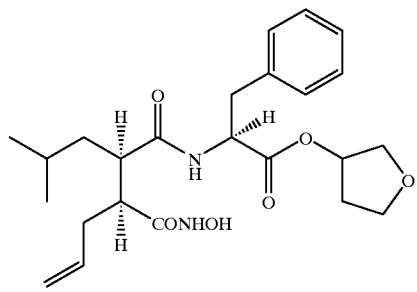

EXAMPLE 35 (Example 36 of WO 98/11063)

2S-(3S-Hydroxycarbamoyl-2R-isobutyl-hex-5-enoylamino)-3,3-dimethyl-butyric acid cyclopentyl ester.

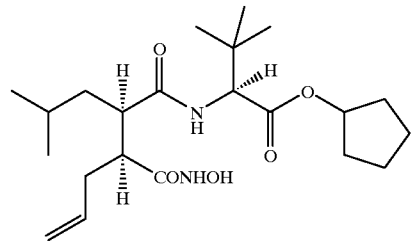

EXAMPLE 36 (Example 37 of WO 98/11063)

2S-[2R-(1S-Cyclopentyl-hydroxycarbamoyl-methyl)-4-methyl-pentanoylamino]-3-phenyl-propionic acid cyclopentyl ester.

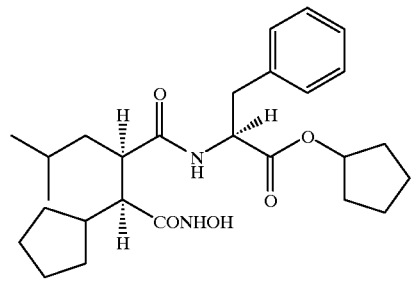

EXAMPLE 37 (Example 38 of WO 98/11063)
2S-[2R-(1S-Hydroxy-hydroxycarbamoyl-methyl)-pent4-ynoylamino]-3-phenylpropionic acid cyclopentyl ester.

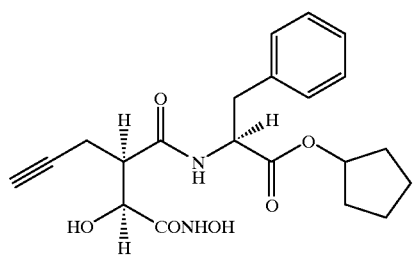

EXAMPLE 38 (Example 39 of WO 98/11063)
2S-(3S-Hydroxycarbamoyl-2R-isobutyl-hex-5-enoylamino)-3-pyridin-3-yl-propionic acid cyclopentyl ester.

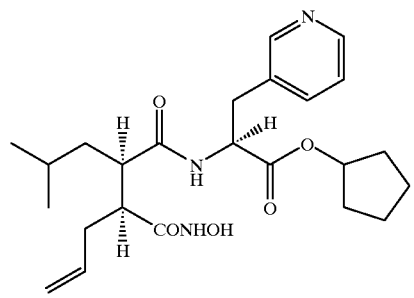

EXAMPLE 39 (Example 40 of WO 98/11063)
3-tert-Butoxy-2S-(3S-hydroxycarbamoyl-2R-isobutyl-hex-5-enoylamino)-propionic acid cyclopentyl ester.

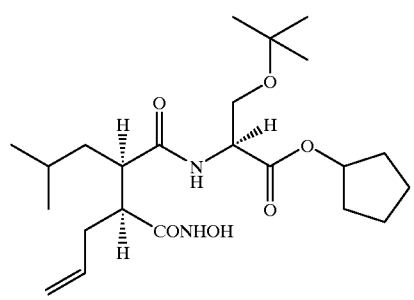

EXAMPLE 40 (Example 41 of WO 98/11063)
2S-(3S-Hydroxycarbamoyl-2R-isobutyl-hex-5-enoylamino)-2-phenylethanoic acid cyclopentyl ester.

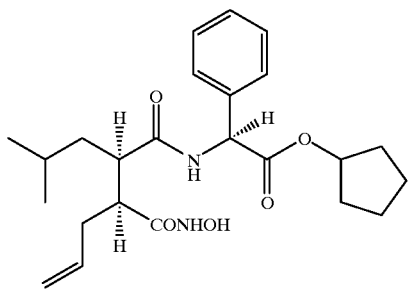

EXAMPLE 41 (Example 42 of WO 98/11063)

2S-[5-(2-Chlorophenyl)-2R-(1S-hydroxy-hydroxycarbamoyl-methyl)-pent-4-ynoylamino]-3-phenylpropionic acid cyclopentyl ester.

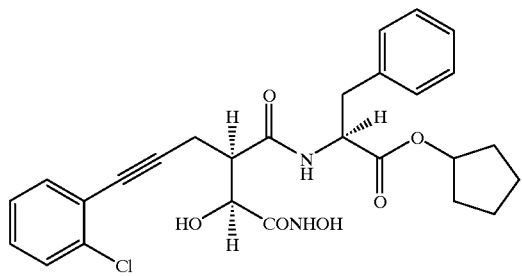

EXAMPLE 42 (Example 43 of WO 98/11063)

2S-(3S-Hydroxycarbamoyl-2R-isobutyl-6-phenyl-hex-5-enoylamino)-3-phenyl-propionic acid cyclopentyl ester.

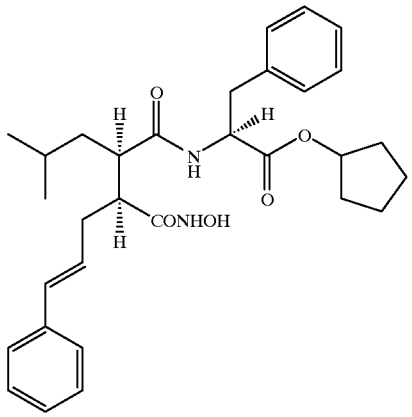

EXAMPLE 43

2-[2R-(S-Hydroxy-hydroxycarbamoyl-methyl)-4-methyl-pentanoylamine]-2-phenyl-ethanoic acid cyclopentyl ester

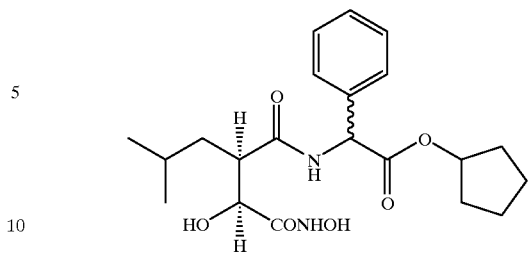

Prepared using procedures similar to those described in example 8 of WO 98/11063, using phenylglycine cyclopentyl ester.

Diastereoisomer A
$^1$H-NMR; δ (MeOD), 7.4–7.29 (5H, m), 5.43 (1H, s), 5.2–5.14 (1H, m), 4.02 (1H, d, J=6.9 Hz), 2.94–2.85 (1H, m), 1.91–1.34 (10H, bm), 1.25–1.14 (1H, m) and 0.86 (6H, dd, J=6.5, 11.5 Hz). $^{13}$C-NMR; δ (MeOD), 175.6, 171.8, 171.4, 137.8, 129.8, 129.4, 128.6, 80.0, 73.2, 58.5, 49.2, 39.1, 33.3, 33.3, 26.8, 24.5, 24.4, 23.7 and 22.1.

Diastereoisomer B
$^1$H-NMR; δ (MeOD), 7.33–7.19 (5H, m), 5.3 (1H, s), 5.11–5.06 (1H, m), 3.81 (1H, d, J=7.3 Hz), 2.83–2.74 (1H, m), 1.83–1.45 (10H, bm), 1.12–1.03 (1H, m) and 0.88–0.81 (6H, dd, J=6.4, 12.3 Hz). $^{13}$C-NMR; δ (MeOD), 175.8, 171.8, 171.5, 137.3, 129.8, 129.5, 128.8, 79.9, 73.3, 58.7, 48.9, 39.2, 33.3, 33.3, 26.7, 24.5, 24.5, 24.0 and 22.2.

EXAMPLE 44

2-(3S-Hydroxycarbamoyl-2R-isobutyl-hex-5-enoylamino)-2-phenylethanoic acid isopropyl ester

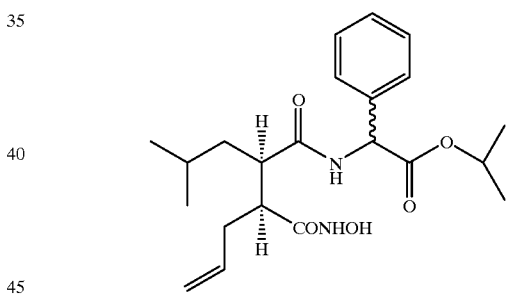

Prepared using methods similar to those described in example 41 of application WO 98/11063 using phenylglycine isopropyl ester.

Diastereoisomer A
$^1$H-NMR; δ (MeOD), 7.34–7.24 (5H, m), 5.59–5.42 (1H, m), 5.36 (1H, s), 5.02–4.77 (3H, m), 2.63–2.53 (1H, m), 2.17–2.02 (2H, m), 1.89–1.78 (1H, m), 1.63–1.45 (2H, m), 1.18 (3H, d, J=6.3 Hz), 1.05 (3H, d, J=6.2 Hz), 1.00–0.93 (1H, m), 0.88 (3H, d, J=6.5 Hz) and 0.81 (3H, d, J=6.5 Hz). $^{13}$C-NMR; δ (MeOD), 176.2, 172.4, 171.3, 137.6, 136.0, 129.9,129.6, 129.0,117.4, 70.5, 58.7,47.4, 41.5, 36.0, 26.7, 24.5, 21.9, 21.7 and 21.7.

Diastereoisomer B
$^1$H-NMR; δ (MeOD), 7.4–7.34 (5H, m), 5.77–5.61 (1H, m), 5.42 (1H, s), 5.1–4.98 (3H, m), 2.7–2.6 (1H, m), 2.44–2.17 (3H, m), 1.61–1.5 (1H, m), 1.42–1.29 (1H, m), 1.25 (3H, d, J=6.3 Hz), 1.13 (3H, d, J=6.2 Hz), 1.09–1.00 (1H, m) and 0.81 (6H, d, J=6.4 Hz). $^{13}$C-NMR; δ (MeOD), 176.4, 172.5, 171.5, 137.2, 136.4, 129.9, 129.6, 129.0, 117.5, 70.5, 58.8, 48.4, 47.4, 41.3, 36.0, 27.1, 24.3, 21.9, 21.8 and 21.6.

EXAMPLE 45
2-[2R-(S-Hydroxycarbamoyl-methoxy-methyl)-4-methyl-pentanoylamino]-3-phenylethanoic acid cyclopentyl ester

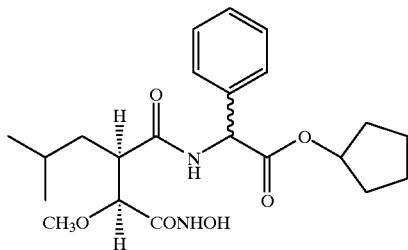

Prepared using methods similar to those described in example 16 of application WO 98/11063, using phenylglycine cyclopentyl ester.

Diastereoisomer A
$^1$H-NMR; δ (MeOD), 8.83 (1H, d, J=6.6 Hz), 7.48–7.29 (5H, m), 5.44–5.42 (1H, m), 5.20–5.16 (1H, m), 3.53 (1H, d, J=9.7 Hz), 3.17 (3H, s), 2.89–2.79 (1H, m), 1.90–1.54 (10H, bm), 1.06–0.99 (1 H, m), 0.95 (3H, d, J=6.5 Hz) and 0.90 (3H, d, J=6.4 Hz). $^{13}$C-NMR; δ (MeOD), 175.3, 171.6, 169.4, 137.5, 129.7, 129.4, 128.7, 83.1, 79.9, 58.7, 58.1, 48.5, 38.4, 33.4, 33.3, 26.7, 24.6, 24.5, 24.3 and 21.8.

Diastereoisomer B
$^1$H-NMR; δ (MeOD), 7.39–7.30 (5H, m), 5.45 (1H, s), 5.21–5.15 (1H, m), 3.59 (1H, d, J=9.4 Hz), 3.29 (3H, s), 2.89–2.79 (1H, m), 1.93–1.49 (9H, bm), 1.42–1.21 (1H, m), 1.01 (1H, ddd, J=3.7, 9.9, 13.3 Hz), 0.83 (3H, d, J=6.5 Hz) and 0.79 (3H, d, J=6.6 Hz). $^{13}$C-NMR; δ (MeOD), 175.1, 171.5, 169.5, 137.9, 129.7, 129.4, 128.7, 83.0, 79.8, 58.5, 58.3, 48.6, 38.5, 33.3, 27.8, 24.5, 24.4, 24.1 and 21.7.

EXAMPLE 46
2-(3S-Hydroxycarbamoyl-2R-isobutyl-hex-5-enoylamino)-2-(4-methoxyphenyl)ethanoic acid cyclopentyl ester

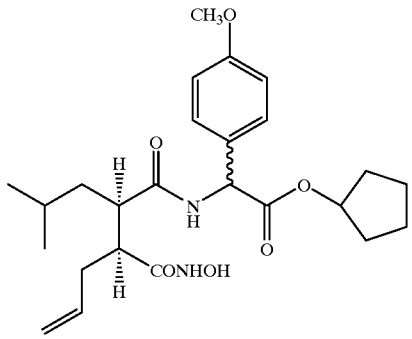

Prepared using methods similar to those described in example 41 of application WO 98/11063, using 4-methoxyphenylglycine cyclopentyl ester.

Diastereoisomer A
$^1$H-NMR; δ (MeOD), 8.94 (1H, d, J=6.4 Hz), 7.32 (2H, d, J=8.7 Hz), 6.93 (2H, d, J=8.7 Hz), 5.67–5.50 (1H, m), 5.36–5.33 (1H, m), 5.20–5.14 (1H, m), 4.93–4.87 (2H, m), 3.79 (3H, s), 2.68–2.59 (1H, m), 2.24–2.09 (2H, m), 1.97–1.55 (11H, bm), 1.11–1.00 (1H, m), 0.95 (3H, d, J=6.5 Hz) and 0.88 (3H, d, J=6.5 Hz). $^{13}$C-NMR; (MeOD), 176.2, 172.4, 171.9, 161.4, 136.0, 130.2, 129.4, 117.4, 115.2, 79.7, 58.2, 55.8, 48.3, 47.3, 41.5, 36.0, 33.4, 33.3, 26.7, 24.6, 24.5 and 21.7.

Diastereoisomer B
$^1$H-NMR; δ (MeOD), 8.96 (1H, d, J=6.7 Hz), 7.29 (2H, d, J=8.7 Hz), 6.93 (2H, d, J=8.7 Hz), 5.77–5.61 (1H, m), 5.32 (1H, s), 5.20–5.15 (1H, m), 5.09–4.97 (2H, m), 3.80 (3H, s), 2.64 (1H, dt, J=3.3, 11.4, 13.5 Hz), 2.43–2.16 (3H, m), 1.91–1.49 (9H, bm), 1.42–1.29 (1H, m), 1.05 (1H, ddd, J=3.3, 10.1, 13.2 Hz) and 0.81 (6H, d, J=6.5 Hz). $^{13}$C-NMR; δ (MeOD), 176.3, 172.5, 172.0, 161.4, 136.4, 130.2, 129.0, 117.5,115.2, 79.8, 58.2, 55.8, 48.4, 47.4, 41.3, 36.1, 33.4, 27.1, 24.5, 24.3 and 21.6.

EXAMPLE 47
2-(3S-Hydroxycarbamoyl-2R-isobutyl-hex-5-enoylamino)-2-(thien-2-yl)ethanoic acid cyclopentyl ester

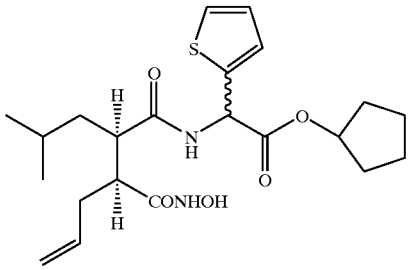

Prepared using methods similar to those described in example 41 of application WO 98/11063, using thien-2-ylglycine cyclopentyl ester.

Diastereoisomer A
$^1$H-NMR; δ (MeOD), 7.41 (1H, dd, J=5.1, 1.2 Hz), 7.12 (1H, d, J=3.5 Hz), 7.01 (1H, dd, J=5.1, 3.5 Hz), 5.72 (1H, s), 5.69–5.52 (1H, m), 5.26–5.18 (1H, m), 5.00–4.89 (2H, m), 2.70–2.59 (1H, m), 2.28–2.13 (2H, m), 2.09–1.50 (11H, m), 1.05 (1H, ddd, J=13.8, 11.0, 2.9 Hz), 0.93 (3H, d, J=6.4 Hz) and 0.87 (3H, d, J=6.5 Hz). $^{13}$C-NMR; δ (MeOD), 176.5, 172.7, 171.1, 139.5, 136.4,128.4, 128.3, 127.7, 117.9, 80.7, 54.1, 48.7, 47.7, 41.9, 36.5, 33.8, 33.7, 27.2, 25.1, 25.0, 24.9, and 22.1.

Diastereoisomer B
$^1$H-NMR; δ (MeOD), 7.42 (1H, dd, J=5.0, 0.7 Hz), 7.10 (1H, d, J=3.6 Hz), 7.01 (1H, dd, J=5.0, 3.6 Hz), 5.79–5.59 (2H, m), 5.28–5.19 (1H, m), 5.10–4.94 (2H, m), 2.71–2.59 (1H, m), 2.36–2.16 (3H, m), 1.97–1.34 (10H, m), 1.13–1.00 (1H, m), 0.86 (3H, d, J=6.2 Hz) and 0.84 (3H, d, J=6.3 Hz). $^{13}$C-NMR; δ (MeOD), 176.7, 172.8, 171.2, 139.3, 136.7, 128.3, 128.2, 127.6, 117.9, 80.7, 54.2, 48.8, 47.8, 41.7, 36.4, 33.8, 27.5, 25.1, 25.0, 24.8 and 22.1.

EXAMPLE 48
2-(3S-Hydroxycarbamoyl-2R-isobutyl-hex-5-enoylamino)-2-(thien-3-yl)ethanoic acid cyclopentyl ester

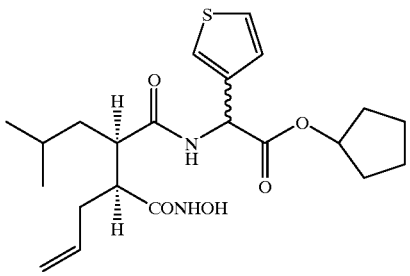

Prepared using methods similar to those described in example 41 of application WO 98/11063, using thien-3-ylglycine cyclopentyl ester.

Diastereoisomer A $^1$H-NMR; δ (MeOD), 7.48–7.42 (2H, m), 7.13 (1H, dd, J=4.2, 2.0 Hz), 5.69–5.52 (2H, m), 5.21–5.16 (1H, m), 4.98–4.90 (2H, m), 2.71–2.59 (1H, m), 2.28–2.11 (2H, m), 2.00–1.50 (11H, m), 1.12–0.98 (1H, m), 0.94 (3H, d, J=6.4 Hz) and 0.88 (3H, d, J=6.5 Hz). $^{13}$C-NMR; δ (MeOD), 176.6, 172.8, 171.8, 137.8, 136.4, 128.3, 128.0, 125.2, 117.9, 80.3, 54.6, 41.9, 36.5, 33.8, 33.8, 27.1, 25.0, 24.9 and 22.1.

Diastereoisomer B $^1$H-NMR; δ (MeOD), 7.45 (1H, dd, J=4.9, 3.0 Hz), 7.43–7.40 (1H, m), 7.12 (1H, dd, J=5.0, 1.3 Hz), 5.68 (1H, ddt, J=17.0, 10.1, 6.8 Hz), 5.53 (1H, s), 5.23–5.17 (1H, m), 5.10–4.96 (2H, m), 2.70–2.60 (1H, m), 2.41–2.16 (3H, m), 1.94–1.49 (9H, m), 1.44–1.29 (1H, m), 1.05 (1H, ddd, J=12.9, 10.3, 3.3 Hz), 0.84 (3H, d, J=6.5 Hz) and 0.83 (3H, d, J=6.5 Hz).

EXAMPLE 49

2S-[2R-(S-Hydroxy-hydroxycarbamoyl-methyl)-3-phenyl-propanoylamine]-2-phenyl-ethanoic acid cyclopentyl ester.

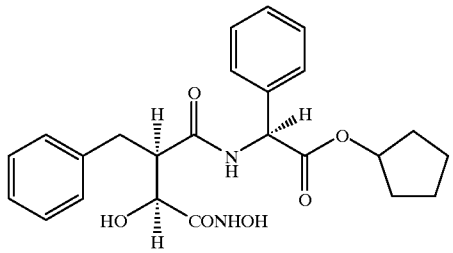

This compound was prepared using the method of example 11 of patent application WO 98/11063 and intermediates similar to those described in patent application WO 95/19956. $^1$H-NMR; δ (MeOD), 7.39–7.15 (10H, m), 5.32 (1H, s), 5,15–5.06 (1H, m), 4.05 (1H, d, J=5.7 Hz), 3.19–3.10 (1H, m), 3.02–2.81 (2H, m) and 1.89–1.40 (8H, m). $^{13}$C-NMR; δ (MeOD), 175.4, 172.1, 171.8, 140.2, 137.9, 130.6, 130.1, 129.9, 129.7, 128.9, 80.4, 72.7, 58.6, 52.4, 36.5, 33.7, 24.9 and 24.8.

EXAMPLE 50

2S-(3S-Hydroxycarbamoyl-2R-cyclopentylmethyl-hex-5-enoylamino)-2-phenyl-ethanoic acid cyclopentyl ester.

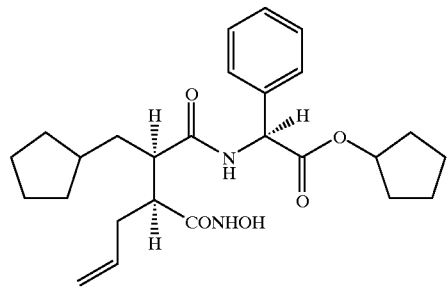

This compound was prepared using the method described for example 1 of patent application WO 98/11063 and intermediates similar to those described in patent application WO 94/21625. $^1$H-NMR; δ (MeOD), 9.02 (1H, m), 7.40 (5H, m), 5.60 (1H, m), 5.45 (1H, m), 5,17 (1H, m), 4.90 (2H, m), 2.61 (1H, m), 2.20 (2H, m), 2.05–1.40 (17H, m) and 1.10 (3H, m).

Biological Example A

Inhibition of Mitogen-induced Lymphocyte Proliferation

The compounds of examples 1, 2, 3, 6, 19, 39, 40 and 43 above were tested for their effects on the proliferation of peripheral blood mononuclear cells (PBMCs) in vitro. The PBMCs were activated with Pokeweed mitogen (PWM), a potent activator of lymphocytes and monocytes which leads to B and T lymphocyte proliferation.

Human PBMCs ($2 \times 10^4$ cells/well), purified from whole blood by centrifugation through ficoll/hypaque, were incubated with PWM (2.5 µg/ml) and compounds 1 and 2 at a range of dilutions in 96 well microtitre plates for 48 hrs at 37° C. in a 5% $CO_2$ incubator. DMSO was run in each assay as a vehicle control. 0.5 µCuries of tritiated thymidine in 40 µl (Amersham) were added to each well during the final 18 hrs. The cells were then harvested on glass fibre pads using a Tomtech cell harvester and, after adding scintillant to the pad (Meltilex) they were placed in a Wallac MicroBeta plate counter. The results obtained are in counts per minute and reflect the level of tritiated thymidine incorporation into the cells and therefore the level of cell proliferation. The percentage proliferation in test wells compared to control wells was calculated and the inhibition curves plotted. The $IC_{50}$ values were calculated from the inhibition curves. All compounds inhibited cell proliferation in a dose related fashion (see Tables 1 and 1 A below).

Biological Example B

Inhibition of Antigen-induced T Lymphocyte Proliferation

The compounds of examples 3, 19 and 1 above were tested for their effects on antigen-driven proliferation of peripheral blood mononuclear cells (PBMCs) in vitro. The PBMCs were activated with Purified protein derivative of Mycobacterium tuberculosis (PPD) which activates PPD (antigen)-specific T lymphocytes. In this system, monocytes are required to internalise and process the antigen and present peptides on MHC class II molecules to PPD-specific T cells for activation in addition to providing co-stimulatory signals to the T cell (B7.1/2, CD40 ligand, etc).

Human PBMCs ($2 \times 10^5$ cells/well), purified from whole blood by centrifugation through ficoll/hypaque, were incubated with PPD (1 µg/ml) and compounds 3, 20 or 1 at a range of dilutions in 96 well microtitre plates for 72 hrs at 37° C. in a 5% $CO_2$ incubator. DMSO was run in each assay as a vehicle control. 0.5 µCuries of tritiated thymidine in 40 µl (Amersham) were added to each well during the final 18 hrs. The cells were then harvested on glass fibre pads using a Tomtech cell harvester and, after adding scintillant to the pad (Meltilex) they were placed in a Wallac MicroBeta plate counter. The results obtained are in counts per minute and reflect the level of tritiated thymidine incorporation into the cells and therefore the level of cell proliferation. The percentage proliferation in test wells compared to control wells was calculated. The data was plotted and the $IC_{50}$ values estimated. All three compounds inhibited cell proliferation in a dose related fashion (see Table 1 below)

Biological Example C

Inhibition of Anti-CD3-induced T Lymphocyte Activation and Proliferation

The compounds of examples 1, 6, 19, 39, 40 and 43 above were tested for its effects on anti-CD3-driven proliferation of peripheral blood mononuclear cells (PBMCs) in vitro. The PBMCs were activated with anti-CD3 antibody which directly activates T lymphocytes via the T cell receptor CD3 component, although other cells do contribute to T cell proliferation by co-stimulation and growth factor production. Human PBMCs ($5 \times 10^4$ cells/well), purified from whole blood by centrifugation through ficoll/hypaque, were incubated in monoclonal anti-CD3 antibody-coated wells (5 $\mu$g/ml) and compound 1 at a range of dilutions in a 96 well microtitre plate for 48 hrs at 37° C. in a 5% $CO_2$ incubator. DMSO was run in each assay as a vehicle control. 0.5 $\mu$Curies of tritiated thymidine in 40 $\mu$l (Amersham) were added to each well during the final 18 hrs. The cells were then harvested on glass fibre pads using a Tomtech cell harvester and, after adding scintillant to the pad (Meltilex) they were placed in a Wallac MicroBeta plate counter. The results obtained are in counts per minute and reflect the level of tritiated thymidine incorporation into the cells and therefore the level of cell proliferation. The percentage proliferation in test wells compared to control wells was calculated. The results were plotted and the $IC_{50}$ value calculated. The compounds inhibited cell proliferation in a dose related fashion (see Tables 1 and 1 A below).

CD69 is a membrane marker of T cell activation. The level of CD69 expression on the membranes of T cells activated by anti-CD3 was therefore measured by fluorescence activated cell (FACS) flow cytometry. PBMCs treated with the compound of example 1 for 4 hrs showed reduced expression of CD69 (48% of T cells) compared to untreated cells (68%). This demonstrates a significant reduction in T cell activation.

TABLE 1

| PBMCs stimulated with: | $IC_{50}$ ($\mu$M) | | | |
| --- | --- | --- | --- | --- |
| | EXAMPLE 1 | EXAMPLE 2 | EXAMPLE 3 | EXAMPLE 19 |
| PWM | 4.7 | 4.8 | 2.4 | not tested |
| PPD | 2.0 | not tested | 1.8 | 1.1 |
| ANTI-CD3 | 2.1 | not tested | not tested | not tested |

TABLE 1A

| COMPOUNDS | PBMCs STIMULATED WITH PWM IC50 ($\mu$M) | PBMCs STIMULATED WITH ANTI-CD3 IC50 ($\mu$M) |
| --- | --- | --- |
| EXAMPLE 19 | 2.1 | 0.9 |
| EXAMPLE 6 | 5.9 | 6.0 |
| EXAMPLE 43 | 2.4 | 4.9 |
| EXAMPLE 39 | 2.8 | 1.8 |
| EXAMPLE 40 | 0.9 | 1.8 |

Biological Example D
Inhibition of Production of TNF

The compound of example 3 above was tested for its effect on the production of the pro-inflammatory cytokine TNF. TNF is released from various cells (monocytes and B lymphocytes) following activation by mitogen or antigen. The production of this inflammatory mediator in the supernatant of activated PBMCs was measured by ELISA.

Human PBMCs ($2-5\times10^6$ cells/well), purified from whole blood by centrifugation through ficoll/hypaque, were incubated with either PWM (2.5 $\mu$g/ml) or PPD (1 $\mu$g/ml) and compound example 3 at 10 $\mu$M in a 24 well microtitre plates for 48 hrs at 37° C. in a $CO_2$ incubator. DMSO was run in each assay as a vehicle control. Supernatant was removed after 48 hrs and microfuged at 10,000 rpm for 2 minutes. Supernatant was removed, aliquotted and stored at $-70°$ C. until tested. The level of TNF was measured by ELISA (R&D Sytems) and the results are shown in Table 2 below.

TABLE 2

| | ACTIVATED PWM TNF (pg/ml) | ACTIVATED PPD TNF (pg/ml) |
| --- | --- | --- |
| example 3 | 495 | 15 |
| dmso | 1390 | 50 |

The compound of example 3 reduced the level of TNF production by 64% in the PWM system and 70% in the PPD system.

In a modification of the above procedure, the compounds of Examples 19 and 40 were tested at 10 $\mu$M for inhibition of TNF production in PWM-activated whole blood diluted 1/5 in RPMI containing 1% nutridoma. The supernatants were tested after 24 hours of culture. The results are shown in Table 3, from which it can be seen that both test compounds reduced the level of TNF production.

TABLE 3

| COMPOUNDS (10 $\mu$M) | TNF alpha (pg/ml) |
| --- | --- |
| EXAMPLE 19 | 489 |
| EXAMPLE 40 | 600 |
| VEHICLE | 1031 |

Biological Example E

The compound of Example 19 above was tested in an animal model of autoimmune disease, known as Experimental Autoimmune Neuritis.

Male Lewis rats were inoculated with bovine myelin (10 mg.kg$^{-1}$) in Freunds adjuvant supplemented with Mycobacterium tuberculosis (7.5 mg.kg$^{-1}$) subcutaneously at the base of the tail. Animals were randomized by bodyweight into groups of 9. Dosing with the test compound (100 mg.kg$^{-1}$ ip uid) or vehicle commenced on day 1 post-inoculation and continued through to day 14, the study ending on day 15. Animals were weighed daily, and from day 9 onwards they were assessed using a clinical scoring system which reflects the severity of paralysis.

At day 15 post-inoculation there was a 93% reduction in mean clinical score of the drug treated group when compared to the vehicle group.

What is claimed is:

1. A method for treatment of mammals suffering from a diseases responsive to inhibition of monocyte and/or macrophage and/or lymphocyte activation and of lymphocyte proliferation, comprising administering to the mammal suffering such disease an amount of a compound of general formula (I) or a pharmaceutically acceptable salt hydrate or solvate thereof sufficient to inhibit such activation and/or proliferation:

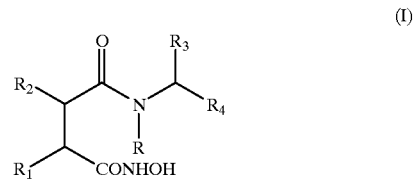

(I)

wherein

R is hydrogen or $(C_1-C_6)$alkyl;

R$_1$ is hydrogen;
  (C$_1$–C$_6$)alkyl;
  (C$_2$–C$_6$)alkenyl;
  phenyl or substituted phenyl;
  phenyl (C$_1$–C$_6$)alkyl or substituted phenyl(C$_1$–C$_6$)alkyl;
  phenyl (C$_2$–C$_6$)alkenyl or substituted phenyl(C$_2$–C$_6$)alkenyl
  heterocyclyl or substituted heterocyclyl;
  heterocyclyl(C$_1$–C$_6$)alkyl or substituted heterocyclyl (C$_1$–C$_6$)alkyl;
  a group BSO$_n$A- wherein n is 0, 1 or 2 and B is hydrogen or a (C$_1$–C$_6$) alkyl, phenyl, substituted phenyl, heterocyclyl substituted heterocyclyl, (C$_1$–C$_6$)acyl, phenacyl or substituted phenacyl group, and A represents (C$_1$–C$_6$)alkylene;
  hydroxy or (C$_1$–C$_6$)alkoxy;
  amino, protected amino, acylamino, (C$_1$–C$_6$) alkylamino or di-(C$_1$–C$_6$)alkylamino;
  mercapto or (C$_1$–C$_6$)alkylthio;
  amino(C$_1$–C$_6$)alkyl, (C$_1$–C$_6$)alkylamino(C$_1$–C$_6$)alkyl, di(C$_1$–C$_6$)alkylamino(C$_1$–C$_6$)alkyl, hydroxy(C$_1$–C$_6$) alkyl, morcapto(C$_1$–C$_6$)alkyl or carboxy(C$_1$–C$_6$) alkyl wherein the amino-, hydroxy-, mercapto- or carboxyl-group are optionally protected or the carboxyl-group amidated;
  lower alkyl substituted by carbamoyl, mono(lower alkyl)carbamoyl, di(lower alkyl)carbamoyl, di(lower alkyl)amino, or carboxy-lower alkanoylamino; or
  a cycloalkyl, cycloalkenyl or non-aromatic heterocyclic ring containing up to 3 heteroatoms, any of which may be (i) substituted by one or more substituents selected from C$_1$–C$_6$ alkyl, C$_2$–C$_6$ alkenyl, halo, cyano (—CN), —CO$_2$H, —CO$_2$R, —CONH$_2$, —CONHR, —CON(R)$_2$, —OH, —OR, oxo-, —SH, —SR, —NHCOR, and —NHCO$_2$R wherein R is C$_1$–C$_6$ alkyl or benzyl and/or (ii) fused to a cycloalkyl or heterocyclic ring;

R$_2$ is a C$_1$–C$_{12}$ alkyl,
  C$_2$–C$_{12}$ alkenyl,
  C$_2$–C$_{12}$ alkynyl,
  phenyl(C$_1$–C$_6$ alkyl)-,
  heteroaryl(C$_1$–C$_6$ alkyl)-,
  phenyl(C$_2$–C$_6$ alkenyl)-,
  heteroaryl(C$_2$–C$_6$ alkenyl)-,
  phenyl(C$_2$–C$_6$ alkynyl)-,
  heteroaryl(C$_2$–C$_6$ alkynyl)-,
  cycloalkyl(C$_1$–C$_6$ alkyl)-,
  cycloalkyl(C$_2$–C$_6$ alkenyl)-,
  cycloalkyl(C$_2$–C$_6$ alkynyl)-,
  cycloalkenyl(C$_1$–C$_6$ alkyl)-,
  cycloalkenyl(C$_2$–C$_6$ alkenyl)-,
  cycloalkenyl(C$_2$–C$_6$ alkynyl)-,
  phenyl(C$_1$–C$_6$ alkyl)O(C$_1$–C$_6$ alkyl)-, or
  heteroaryl(C$_1$–C$_6$ alkyl)O(C$_1$–C$_6$ alkyl)-group,
  any one of which may be optionally substituted by
    C$_1$–C$_6$ alkyl,
    C$_1$–C$_6$ alkoxy,
    halo,
    cyano (—CN),
    phenyl or heteroaryl, or
    phenyl or heteroaryl substituted by
      C$_1$–C$_6$ alkyl,
      C$_1$–C$_6$ alkoxy,
      halo, or
      cyano (—CN);

R$_3$ is the characterising group of a natural or non-natural α amino acid in which any functional groups may be protected; and R$_4$ is an ester or thioester group.

2. The use of a compound of formula (I) as defined in claim 1 in the preparation of a composition for treatment of mammals suffering from a disease responsive to inhibition of monocyte and/or macrophage and/or lymphocyte activation and of lymphocyte proliferation.

3. A method as claimed in claim 1 wherein the stereochemical configuration of the carbon atom carrying the group R$_2$ is R, and that of the carbon atom carrying the groups R$_3$ and R$_4$ is S.

4. A method as claimed in claim 1 wherein R$_1$ is:
  hydrogen, methyl, ethyl, n-propyl, n-butyl, isobutyl, hydroxyl, methoxy, allyl, phenylpropyl, phenylprop-2-enyl, thienylsulphanylmethyl, thienylsulphinylmethyl, or thienylsulphonylmethyl; or
  C$_1$–C$_4$ alkyl, eg methyl, ethyl n-propyl or n-butyl, substituted by a phthalimido, 1,2-dimethyl-3,5-dioxo-1,2,4-triazolidin-4-yl, 3-methyl-2,5-dioxo-1-imidazolidinyl, 3,4,4-trimethyl-2,5-dioxo-1-imidazolidinyl, 2-methyl-3,5-dioxo-1,2,4-oxadiazol-4-yl, 3-methyl-2,4,5-trioxo-1-imidazolidinyl, 2,5-dioxo-3-phenyl-1-imidazolidinyl, 2-oxo-1-pyrrolidinyl, 2,5-dioxo-1-pyrrolidinyl or 2,6-dioxopiperidinyl, 5,5-dimethyl-2,4-dioxo-3-oxazolidinyl, hexahydro-1,3-dioxopyrazolo[1,2,a][1,2,4]-triazol-2-yl, or a naphththalimido (ie 1,3-dihydro-1,3-dioxo-2H-benz[f]isoindol-2-yl), 1,3-dihydro-1-oxo-2H-benz[f]isoindol-2-yl, 1,3-dihydro-1,3-dioxo-2H-pyrrolo[3,4-b]quinolin-2-yl, or 2,3-dihydro-1,3-dioxo-1H-benz[d,e]isoquinolin-2-yl group; or
  cyclohexyl, cyclooctyl, cycloheptyl, cyclopentyl, cyclobutyl, cyclopropyl, tetrahydropyranyl or morpholinyl.

5. A method as claimed in claim 1 wherein R$_1$ is n-propyl, allyl, hydroxy, methoxy and thienylsulfanylmethyl.

6. A method as claimed in claim 1 or the use as claimed in claim 2 wherein R$_2$ is:
  C$_1$–C$_{12}$ alkyl, C$_3$–C$_6$ alkenyl or C$_3$–C$_6$ alkynyl;
  phenyl(C$_1$–C$_6$ alkyl)-, phenyl(C$_3$–C$_6$ alkenyl)- or phenyl (C$_3$–C$_6$ alkynyl)- optionally substituted in the phenyl ring;
  heteroaryl(C$_1$–C$_6$ alkyl)-, heteroaryl(C$_3$–C$_6$ alkenyl)- or heteroaryl(C$_3$–C$_6$ alkynyl)- optionally substituted in the heteroaryl ring;
  4-phenylphenyl(C$_1$–C$_6$ alkyl)-, 4-phenylphenyl(C$_3$–C$_6$ alkenyl)-, 4-phenylphenyl(C$_3$–C$_6$ alkynyl)-, 4-heteroarylphenyl(C$_1$–C$_6$ alkyl)-, 4-heteroarylphenyl (C$_3$–C$_6$ alkenyl)-, 4-heteroarylphenyl(C$_3$–C$_6$ alkynyl)-, optionally substituted in the terminal phenyl or heteroaryl ring; or
  phenoxy(C$_1$–C$_6$ alkyl)- or heteroaryloxy(C$_1$–C$_6$ alkyl)- optionally substituted in the phenyl or heteroaryl ring.

7. A method as claimed in claim 1 wherein R$_2$ is: methyl, ethyl, n- or iso-propyl, n-, iso- or tert-butyi, n-pentyl, n-hexyl, n-heptyl, n-nonyl, n-decyl, prop-2-yn-1-yl, 3-phenylprop-2-yn-1-yl, 3-(2-chlorophenyl)prop-2-yn-1-yl, phenylpropyl, 4-chlorophenylpropyl, 4-methylphenylpropyl, 4-methoxyphenylpropyl, phenoxybutyl, 3-(4-pyridylphenyl)propyl-, 3-(4-(4-pyridyl) phenyl)prop-2-yn-1-yl, 3-(4-phenylphenyl)propyl-, 3-(4-phenyl)phenyl)prop-2-yn-1-yl, or 3-[(4-chlorophenyi) phenyl]propyl-.

8. A method as claimed in claim 1 wherein R$_2$ is n- or iso-butyl, n-hexyl, cyclopentylmethyl, benzyl, and 3-(2-chlorophenyl)prop-2-yn-1-yl.

9. A method as claimed in claim 1 wherein R$_3$ is C$_1$–C$_6$ alkyl, phenyl, 2-, 3-, or 4-hydroxyphenyl, 2-, 3-, or 4-methoxyphenyl, 2- or 3-thienyl, 2-, 3-, or 4-pyridylmethyl, benzyl, 2-, 3-, or 4-hydroxybenzyl, 2-, 3-, or 4-benzyloxybenzyl, 2-, 3-, or 4-$C_1$–$C_6$ alkoxybenzyl, or benzyloxy($C_1$–$C_6$alkyl)-.

10. A method as claimed in claim 1 wherein $R_3$ is the characterising group of a natural α amino acid, in which any functional group may be protected, any amino group may be acylated and any carboxyl group present may be amidated.

11. A method as claimed in claim 1 wherein $R_3$ is a group -[Alk]$_n$$R_6$ where Alk is a ($C_1$–$C_6$)alkyl or ($C_2$–$C_6$)alkenyl group optionally interrupted by one or more —O—, or —S— atoms or —N($R_7$)— groups [where $R_7$ is a hydrogen atom or a ($C_1$–$C_6$)alkyl group], n is 0 or 1, and $R_6$ is an optionally substituted cycloalkyl or cycloalkenyl group.

12. A method as claimed in claim 1 wherein $R_3$ is a benzyl group substituted in the phenyl ring by a group of formula —OCH$_2$COR$_8$ where $R_8$ is hydroxyl, amino, ($C_1$–$C_6$) alkoxy, phenyl($C_1$–$C_6$)alkoxy, ($C_1$–$C_6$)alkylamino, di(($C_1$–$C_6$)alkyl)amino, phenyl($C_1$–$C_6$)alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid.

13. A method as claimed in claim 1 wherein $R_3$ is a heterocyclic($C_1$–$C_6$)alkyl group, either being unsubstituted or mono- or di-substituted in the heterocyclic ring with halo, nitro, carboxy, ($C_1$–$C_6$)alkoxy, cyano, ($C_1$–$C_6$)alkanoyl, trifluoromethyl ($C_1$–$C_6$)alkyl, hydroxy, formyl, amino, ($C_1$–$C_6$)alkylamino, di-($C_1$–$C_6$)alkylamino, mercapto, ($C_1$–$C_6$)alkylthio, hydroxy($C_1$–$C_6$)alkyl, mercapto($C_1$–$C_6$) alkyl or ($C_1$–$C_6$)alkylphenylmethyl.

14. A method as claimed in claim 1 wherein $R_3$ is a group —CR$_a$R$_b$R$_c$ in which:

each of $R_a$, $R_b$ and $R_c$ is independently hydrogen, ($C_1$–$C_6$) alkyl, ($C_2$–$C_6$)alkenyl, ($C_2$–$C_6$)alkynyl, phenyl($C_1$–$C_6$) alkyl, ($C_3$–$C_8$)cycloalkyl; or $R_c$ is hydrogen and $R_a$ and $R_b$ are independently phenyl or heteroaryl such as pyridyl; or $R_c$ is hydrogen, ($C_1$–$C_6$)alkyl, ($C_2$–$C_6$)alkenyl, ($C_2$–$C_6$) alkynyl, phenyl($C_1$–$C_6$)alkyl, or ($C_3$–$C_6$)cycloalkyl, and $R_a$ and $R_b$ together with the carbon atom to which they are attached form a 3 to 8 membered cycloalkyl or a 5- to 6-membered heterocyclic ring; or $R_a$, $R_b$ and $R_c$ together with the carbon atom to which they are attached form a tricyclic ring (for example adamantyl); or $R_a$ and $R_b$ are each independently ($C_1$–$C_6$)alkyl, ($C_2$–$C_6$) alkenyl, ($C_2$–$C_6$)alkynyl, phenyl($C_1$–$C_6$)alkyl, or a group as defined for $R_c$ below other than hydrogen, or $R_a$ and $R_b$ together with the carbon atom to which they are attached form a cycloalkyl or heterocyclic ring, and $R_c$ is hydrogen, —OH, —SH, halogen, —CN, —CO$_2$H, ($C_1$–$C_4$)perfluoroalkyl, —CH$_2$OH, —CO$_2$ ($C_1$–$C_6$)alkyl, —O($C_1$–$C_6$)alkyl, —O($C_2$–$C_6$)alkenyl, —S($C_1$–$C_6$)alkyl, —SO($C_1$–$C_6$)alkyl, —SO$_2$($C_1$–$C_6$) alkyl, —S($C_2$–$C_6$)alkenyl, —SO($C_2$–$C_6$)alkenyl, —SO$_2$($C_2$–$C_6$)alkenyl or a group —Q—W wherein Q represents a bond or —O—, —S—, —SO— or —SO$_2$— and W represents a phenyl, phenylalkyl, ($C_3$–$C_8$)cycloalkyl, ($C_3$–$C_8$)cycloalkylalkyl, ($C_4$–$C_8$) cycloalkenyl, ($C_4$–$C_8$)cycloalkenylalkyl, heteroaryl or heteroarylalkyl group, which group W may optionally be substituted by one or more substituents independently selected from, hydroxyl, halogen, —CN, —CO$_2$H, —CO$_2$($C_1$–$C_6$)alkyl, —CONH$_2$, —CONH ($C_1$–$C_6$)alkyl, —CONH($C_1$–$C_6$alkyl)$_2$, —CHO, —CH$_2$OH, ($C_1$–$C_4$)perfluoroalkyl, —O($C_1$–$C_6$)alkyl, —S($C_1$–$C_6$)alkyl, —SO($C_1$–$C_6$)alkyl, —SO$_2$($C_1$–$C_6$) alkyl, —NO$_2$, —NH$_2$, —NH($C_1$–$C_6$)alkyl, —N(($C_1$–$C_6$)alkyl)$_2$, —NHCO($C_1$–$C_6$)alkyl, ($C_1$–$C_6$) alkyl, ($C_2$–$C_6$)alkenyl, ($C_2$–$C_6$)alkynyl, ($C_3$–$C_8$) cycloalkyl, ($C_4$–$C_8$)cycloalkenyl, phenyl or benzyl.

15. A method as claimed in claim 1 wherein $R_3$ is phenyl, benzyl, tert-butoxymethyl or iso-butyl.

16. A method as claimed in claim 1 wherein $R_4$ is a group of formula —(C=O)OR$_9$, —(C=O)SR$_9$, —(C=S)SR$_9$, and —(C=S)OR$_9$ wherein $R_9$ is is ($C_1$–$C_6$)alkyl, ($C_2$–$C_6$) alkenyl, cycloalkyl, cycloalkyl($C_1$–$C_6$)alkyl-, phenyl, heterocyclyl, phenyl($C_1$–$C_6$)alkyl-, heterocyclyl($C_1$–$C_6$) alkyl-, ($C_1$–$C_6$)alkoxy($C_1$–$C_6$)alkyl- or ($C_1$–$C_6$)alkoxy ($C_1$–$C_6$)alkoxy($C_1$–$C_6$)alkyl-, any of which may be substituted on a ring or non-ring carbon atom or on a ring heteroatom, if present.

17. A method as claimed in claim 1 wherein $R_4$ is a group of formula —(C=O)OR$_9$, wherein $R_9$ is methyl, ethyl, n- or iso-propyl, n-, sec- or tert-butyl, 1-ethyl-prop-1-yl, 1-methyl-prop-1-yl, 1-methyl-but-1-yl, cyclopentyl, cyclohexyl, allyl, phenyl, benzyl, 2-, 3- and 4-pyridylmethyl, N-methylpiperidin-4-yl, 1-methylcyclopent-1yl, adamantyl, tetrahydrofuran-3-yl or methoxyethyl.

18. A method as claimed in claim 1 wherein $R_4$ is a group of formula —(C=O)OR$_9$ wherein $R_9$ is benzyl, cyclopentyl, isopropyl or tert-butyl.

19. A method as claimed in claim 1 wherein R is hydrogen or methyl.

20. A method as claimed in claim 1 wherein $R_1$ is n-propyl, allyl, hydroxy, methoxy or thienylsulfanyl-methyl, $R_2$ is isobutyl, n-hexyl, cyclopentylmethyl, benzyl or 3-(2-chlorophenyl)prop-2-yn-1-yl, $R_3$ is phenyl, benzyl, tert-butoxymethyl, n-butyl or iso-butyl, $R_4$ is a group of formula —(C=O)OR$_9$ wherein $R_9$ is benzyl, cyclopentyl, isopropyl or tert-butyl and R is hydrogen or methyl.

21. A method as claimed in claim 1 wherein the compound is ary of those specified in any of the Examples 1 to 50 herein.

22. A method according to claim 1, wherein the disease to be treated is an autoimmune disease, transplant rejection, graft-versus-host disease, pancreatitis, or an allergy.

* * * * *